United States Patent
Higgins, Jr. et al.

(10) Patent No.: US 10,206,608 B2
(45) Date of Patent: Feb. 19, 2019

(54) APPARATUS AND METHODS FOR CALIBRATING AND/OR VALIDATING PULMONARY FUNCTION TEST EQUIPMENT

(71) Applicant: nSpire Health, Inc., Longmont, CO (US)

(72) Inventors: John Francis Higgins, Jr., Henderson, CO (US); Eric Norgard, Louisville, CO (US)

(73) Assignee: nSpire Health, Inc., Longmont, CO (US)

(*) Notice: Subject to any disclaimer, the term of this patent is extended or adjusted under 35 U.S.C. 154(b) by 0 days.

(21) Appl. No.: 15/995,821

(22) Filed: Jun. 1, 2018

(65) Prior Publication Data
US 2018/0344209 A1 Dec. 6, 2018

Related U.S. Application Data

(60) Provisional application No. 62/513,665, filed on Jun. 1, 2017.

(51) Int. Cl.
*G01N 33/00* (2006.01)
*A61B 5/091* (2006.01)
*A61B 5/097* (2006.01)
*A61B 5/08* (2006.01)

(52) U.S. Cl.
CPC ........... *A61B 5/091* (2013.01); *A61B 5/082* (2013.01); *A61B 5/097* (2013.01); *A61B 2560/0223* (2013.01)

(58) Field of Classification Search
CPC . A61B 5/097; A61B 5/082; A61B 2560/0223; A61B 2560/04; A61B 2560/06; G01N 33/006

(Continued)

(56) References Cited

U.S. PATENT DOCUMENTS 4,083,367 A 4/1978 Portner et al.
5,022,406 A 6/1991 Tomlinson
(Continued)

FOREIGN PATENT DOCUMENTS

CN 102715904 A 10/2012
DE 10038818 A1 2/2002
EP 1109018 A2 6/2001

OTHER PUBLICATIONS

Extended European Search Report issued by the European Patent Office for Application No. 13193202.2, dated Feb. 20, 2014, 7 pages.
(Continued)

*Primary Examiner* — Robert R Raevis
(74) *Attorney, Agent, or Firm* — Cooley LLP

(57) ABSTRACT

The present invention relates to quality control of pulmonary function test (PFT) devices. In particular, but not by way of limitation, the present invention relates to systems and methods for characterizing or verifying the measurement accuracy of pulmonary function testing devices used for measuring dynamic lung volumes (tidal volume (TV), inspiratory reserve volume (IRV), expiratory reserve volume (ERV), divisions thereof, and any other suitable dynamic lung volume) using spirometry, static and/or absolute lung volumes (total lung capacity (TLC), residual volume (RV), divisions thereof, and any other suitable absolute lung volume) using washout, dilution, and/or plethysmographic methods, and/or gas exchange, such as single-breath determination of carbon monoxide uptake in the lung ($D_{LCO}$).

28 Claims, 10 Drawing Sheets

(58) Field of Classification Search
USPC ..... 73/1.02–1.07, 1.19–1.23, 864.11–864.21, 73/865.6; 422/501, 512–519, 521–526
See application file for complete search history.

(56) References Cited

U.S. PATENT DOCUMENTS

| | | | |
|---|---|---|---|
| 5,193,551 | A | 3/1993 | Pilipski |
| 6,139,506 | A | 10/2000 | Heinonen |
| 6,415,642 | B1 | 7/2002 | Crapo et al. |
| 7,114,367 | B1 | 10/2006 | Owens |
| 8,721,561 | B2 | 5/2014 | Thomas et al. |
| 9,186,090 | B2 | 11/2015 | Chu et al. |
| 2009/0038371 | A1 | 2/2009 | Verbraak et al. |

OTHER PUBLICATIONS

First Office Action issued by the Chinese Patent Office for Application No. 201310721712.8, dated Mar. 31, 2017, 18 pages. (includes English translation).

Graham BL, Brusasco V, Burgos F, et al., "2017 ERS/ATS standards for single-breath carbon monoxide uptake in the lung," Eur Respir J 2017; 49: 1600016 [https://doi.org/10.1183/13993003.00016-2016], 31 pages.

Jensen et al., "Instrument Accuracy and Reproducibility in Measurements of Pulmonary Function," CHEST 132(2):388-395 (2007).

Jensen et al., "Quality control of DL,CO instruments in global clinical trials," European Respiratory Journal 33(4):828-834 (2009).

Miller et al., "Series "ATS/ERS Task Force: Standardisation of Lung Function Testing, General considerations for lung function testing" Edited by V. Brusasco, R. Crapo and G. Viegi No. 1 in this Series," Eur Respir J 26: 153-161 (2005).

Miller et al., "Series ATS/ERS Task Force: Standardisation of Lung Function Testing" Edited by V. Brusasco, R. Crapo and G. Viegi No. 2 in this Series Standardisation of spirometry Eur Respir J 26: 319-338 (2005).

Non-Final Office Action issued by The United States Patent and Trademark Office for U.S. Appl. No. 13/682,199, dated Dec. 5, 2014, 9 pages.

Wanger et al., "Series "ATS/ERS Task Force: Standardisation of Lung Function Testing" Edited by V. Brusasco, R. Crapo and G. Viegi No. 3 in this Series Standardisation of the measurement of lung volumes," Eur Respir J 26: 511-522 (2005).

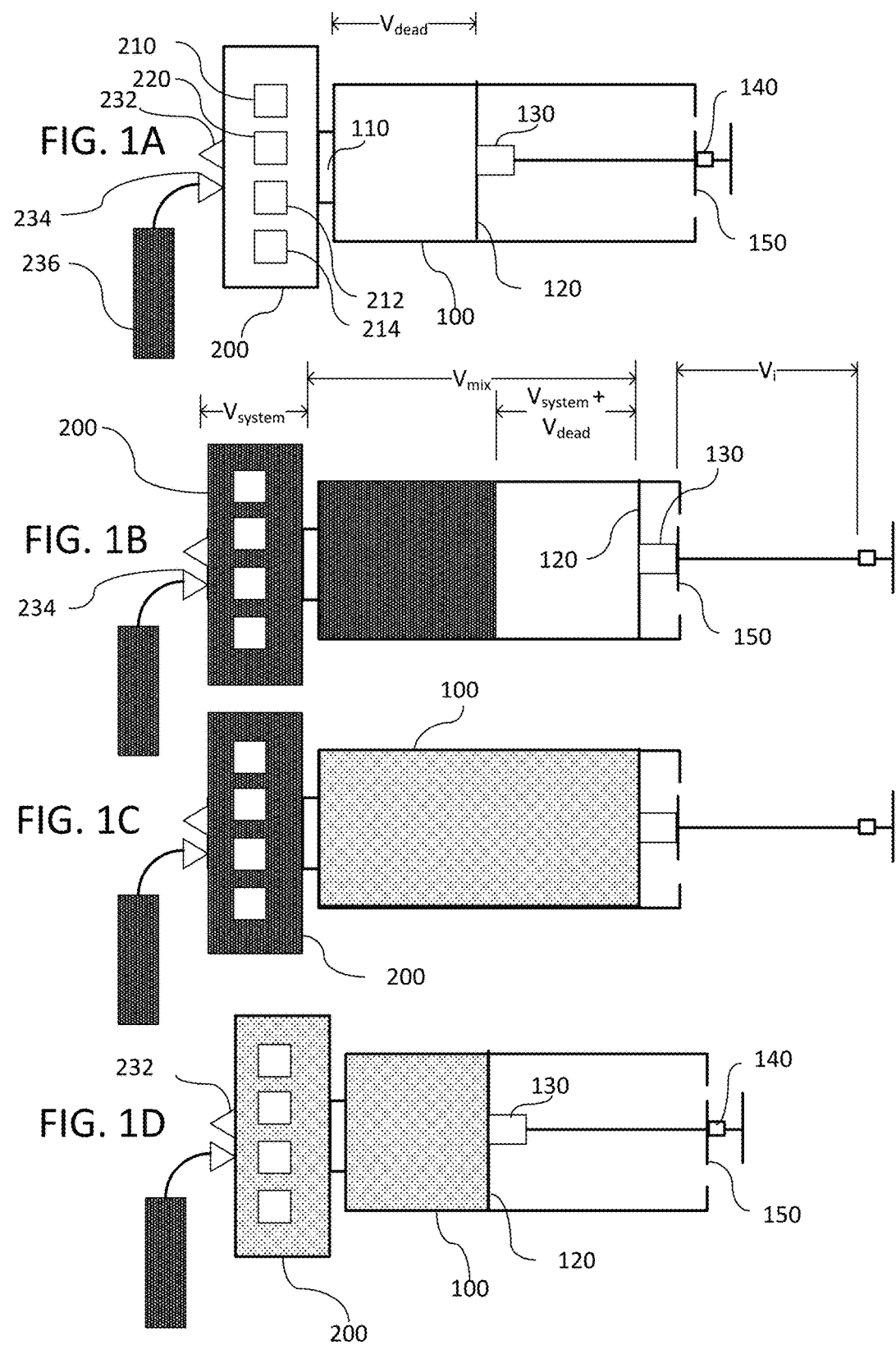

APPARATUS AND METHODS FOR CALIBRATING AND/OR VALIDATING PULMONARY FUNCTION TEST EQUIPMENT

CROSS REFERENCE TO RELATED APPLICATIONS

This application is a non-provisional of, and claims the benefit of priority of U.S. Provisional Patent Application No. 62/513,665, filed Jun. 1, 2017, entitled "Apparatus and Method for Calibrating and/or Validating Pulmonary Function Test Equipment," the disclosure of which is hereby incorporated by reference in its entirety.

FIELD OF THE INVENTION

The present invention relates to quality control of pulmonary function test (PFT) devices. In particular, but not by way of limitation, the present invention relates to systems and methods for characterizing or verifying the measurement accuracy of pulmonary function testing devices used for measuring dynamic lung volumes (tidal volume (TV), inspiratory reserve volume (IRV), expiratory reserve volume (ERV), divisions thereof, and any other suitable dynamic lung volume) using spirometry, static and/or absolute lung volumes (total lung capacity (TLC), residual volume (RV), divisions thereof, and any other suitable absolute lung volume) using washout, dilution, and/or plethysmographic methods, and/or gas exchange, such as single-breath determination of carbon monoxide uptake in the lung ($D_{LCO}$).

BACKGROUND

Performing a pulmonary function test (PFT) generally involves the use of instrumentation operable to measure physiologic respiratory volume(s) and/or respiratory gas exchange. PFT instruments (also referred to herein as PFT equipment or devices) can include testing capability for dynamic lung volumes, static and/or absolute lung volumes (and related parameters) using washout, dilution, and/or plethysmographic methods, and/or measures of gas exchange such as calculated transfer factor ($D_{LCO}$) and related primary measured parameters and related physiologic tests. Spirometry parameters are typically measured with gas flow sensors using a variety of technologies. In the case of washout techniques, static and absolute lung volume parameters are typically measured with gas analyzers measuring inhaled and exhaled $CO_2$ and $O_2$ gas concentrations in conjunction with the aforementioned gas flow measurements.

Plethysmographic methods of measuring static and absolute lung volume parameters typically utilize flow and pressure sensors. Calculation of gas exchange parameters are based on gas analyzer measurements of inhaled and exhaled CO and a non-diffusing tracer gas, such as $CH_4$ or He, in conjunction with the aforementioned gas flow measurements. Commercially available PFT instruments used for static lung volume and/or gas exchange measurements typically provide a test gas from a high-pressure source that is regulated to atmospheric pressure for delivery to patients using a regulator (e.g., a demand valve).

To assure accurate and/or precise measurements, it is desirable to verify and/or calibrate PFT instruments periodically and/or prior to patient use. Such verification and/or calibration can serve to confirm, for example, that the PFT instrument conforms to the stated manufacturer's performance specifications. The present application relates generally to a means and apparatus to verify and/or calibrate a PFT instrument to its stated manufacturer's specifications in a clinical environment.

Verifying PFT instrumentation generally refers to subjecting the instrument to a known standard, reference volume, and/or known standard, reference concentration, of test gases, including air at ambient temperature and pressure, and verifying that the PFT equipment returns a value consistent with the known volume reference and/or known gas concentration reference.

Calibrating PFT instrumentation generally refers to adjusting parameters of the PFT instrument in response to subjecting the PFT instrument to a known standard volume and/or known standard concentrations of a test gases such that the PFT instrument returns a value consistent with the known volume and/or gas concentration. Commonly available PFT instruments are typically calibrated at the time of manufacture and/or by trained service technicians and verified by end-users and/or medical professionals under normal operating conditions in the patient testing environment.

It is further desirable for PFT instruments to verifiably provide physiologically and/or clinically representative data. To verify that PFT instruments have sufficient accuracy and/or precision to provide physiologically representative and/or clinically meaningful data, it is desirable to calibrate and/or validate PFT instruments to minimum clinical accuracy requirements such as those set by peer societies, in particular the Joint American Thoracic Society and European Respiratory Society guidelines for the standardization of lung function testing in the patient testing (clinical) environments.

Generally, validation and/or calibration techniques applied to PFT instruments involves passing a known volume of gas and/or one or more gas mixtures having a known concentration or ratio of concentrations of a test gas to the PFT instrument. Existing methods for validating and/or calibrating PFT instruments include:

1. Utilizing a person with a known transfer capacity as a measurement reference.
2. Utilizing a device that delivers known gas volumes and/or at least two gas mixtures from individual sources having differing, but known, concentrations of a test gas.
3. Utilizing a device that delivers known gas volumes and at least two gas mixtures having known concentrations of the test gas by diluting one gas mixture into another. For example, U.S. Pat. No. 9,186,090, which is hereby incorporated by reference in its entirety, describes some methods and apparatus for diluting one gas mixture into another to validate and/or calibrate $D_{LCO}$ capable PFT equipment.

Such methods are generally unable to calibrate and/or validate PFT instruments to minimum clinical standards and/or manufacturers' specifications, particularly in a clinical environment.

Regarding spirometry measurements: current minimum clinical volume accuracy requirements of PFT instruments requires measured volumes be within +/−2% or 50 mL (whichever is greater) of expected over a volume range of 0.5 L to 8 L and within flow rates up to 14 L/Sec. The current industry standard volume reference used to verify PFT instruments in the field is a gas syringe that displaces relatively large volumes of gas, such as three to nine liters of gas. During verification or calibration procedures, the syringe is commonly subject to heating and cooling sources typically found in patient testing environments, such as HVAC, direct sunlight, or body heat from direct contact of a user. Consequently, using existing devices and practices, the volume delivered by the syringe deviates from its certified value to levels that render it insufficient to verify the manufacturer's specifications or minimal clinical accuracy requirements, whichever is better. For example, a temperature difference of as little as 3° C. between the gas temperature within the volume reference standard device and ambient gas temperature will introduce an error of approximately 1% into the reference volume.

Regarding absolute and static lung volume measurements utilizing nitrogen washout methods: current minimum clinical volume accuracy requirements of PFT instruments requires measured volume accuracies commensurate with spirometry as described above while delivering $O_2$ test gas at atmospheric pressure to a patient. Accuracy of current volume reference standards are subject to the same limitations as described above. A further limitation is that existing volume reference standards do not provide a physiologically representative dynamic compliance as a load to the PFT instrument when inspiring test gas from a regulated high-pressure gas source, which can render the simulated PFT volume measurement invalid, regardless of its delivered volume accuracy.

Regarding gas exchange measurements: current minimum clinical volume accuracy requirements of PFT instruments measuring single-breath determination of carbon monoxide uptake in the lung ($D_{LCO}$) are commensurate with the standards for absolute and static lung volume measurements as described above. In addition to the volume accuracy requirements, achieving the clinical accuracy requirements of the $D_{LCO}$ parameter (+/-2 mL/min/mmHg @2σ) requires gas analyzer measurements to be linear within +−0.75% of their full scale range. The gas analyzer linearity requirement applies to physiological ranges of use, which typically are 50% to 80% of full-scale concentration for the tracer gas (e.g., $CH_4$ or He) and 30% to 50% of full-scale concentration of CO gas, subject to variations in field operating conditions as previously described. Typically, linearity of gas analyzers is validated and/or calibrated using several standard gases having different concentrations of the gas under test. Pre-mixed precision gas mixtures suitable for calibrating and/or validating gas analyzers with suitable accuracy to meet the manufacturer's specifications and/or clinical accuracy requirements of the $D_{LCO}$ parameter, are not, however, available and/or are extremely expensive.

Furthermore, reference standards (e.g., syringes) are generally unable to provide sufficiently accurate ratiometric gas concentrations to verify minimal gas analyzer linearity requirements, whether delivered by gas dilution methods or from methods utilizing multiple gas sources. For example, the mixing ratio of a dilution syringe can theoretically be indirectly determined by measuring relevant volumes of a dilution syringe with water and a suitable NIST traceable scale. However, the actual geometry and construction of dilution syringes can render such a theoretical approach unsatisfactory in practice. In particular, it can be challenging or impossible to eliminate air pockets from within the syringe, valve-less diffusion barriers have no defined boundary to water measure, and valve-based diffusion barriers may not be openable without disassembly or modification. Because of the deficiencies of currently existing standards and methods to calibrate and/or validate PFT instruments to manufacturers' specifications and/or minimum clinical standards in a clinical environment, a need for improved methods and devices for calibrating and/or validating PFT instruments is needed. Such improved methods and devices can be operable to produce PFT instruments with improved accuracy and/or precision.

Some methods and apparatus described herein may be suitable to calibrate and/or validate PFT devices according to at least manufacturer's specifications and/or current minimum clinical standards/requirements. Methods and apparatus described herein may also be suitable to calibrate and/or validate PFT equipment to levels of accuracy and/or precision beyond current minimum clinical standards/requirements and/or may be suitable to calibrate and/or validate PFT equipment under variable field operating conditions (including, for example, ambient temp changes of up to 15° C. and operator induced variability).

BRIEF DESCRIPTION OF THE DRAWINGS

FIGS. 1A-1D depict a syringe in various configurations and a PFT device, according to an embodiment.

DETAILED DESCRIPTION

Figure 2A:
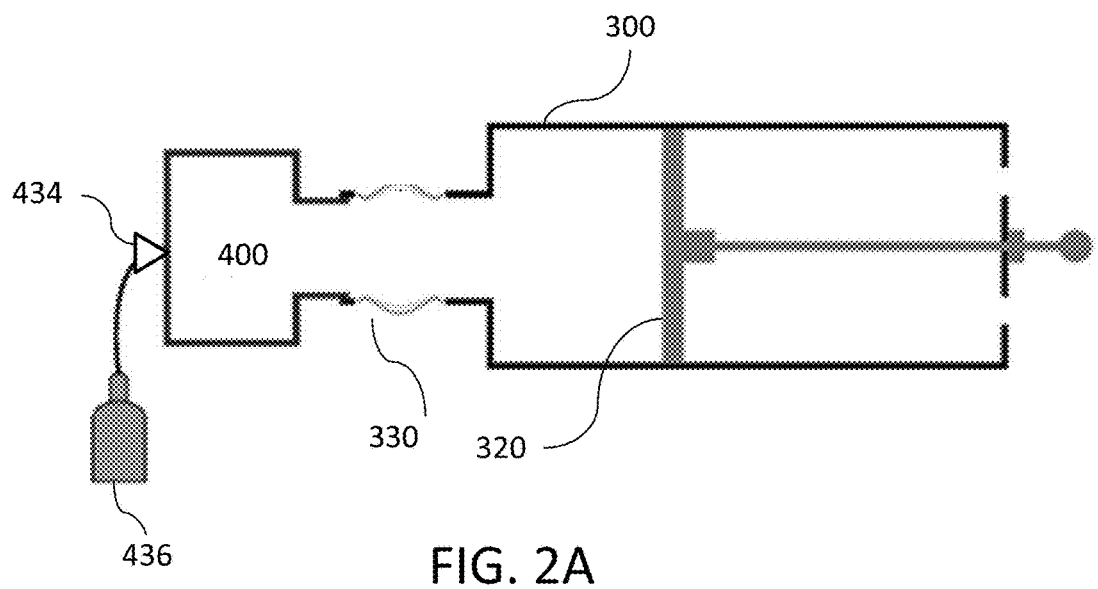
FIG. 2A is a schematic illustration of a syringe and a PFT device, according to an embodiment.

Some embodiments described herein relate to systems and methods for validating and/or calibrating volume measurements of PFT systems using non-pressurized ambient gas using flow technologies in a clinical environment. Such systems and methods can use a syringe to provide a known or standard volume of gas to a PFT instrument. Some existing syringes used as gas volume standards are specified with a ±0.5% relative volume accuracy. This represents a quarter of the total error allowanced for some flow sensors used for PFT tests that measure flow and/or volume. Although some existing syringes are theoretically suitable to deliver a volume of gas with ±0.5% accuracy under ideal operating conditions, in practice, achieving ±0.5% accuracy in terms of gas volume requires the cylinder temperature to match ambient to within 1° C. or less. The isothermal ideal gas law, PV=nRT, states that a gas volume or pressure will change proportionally to its absolute temperature. Any gas entering the syringe cylinder will expand or contract if the temperature of the cylinder differs from the gas temperature. Under the most common use case, the body temperature of a user is approximately 10° C. higher than the temperature of the syringe cylinder. Placing a hand on the cylinder during use or cradling the syringe can heat the cylinder multiple degrees Celsius above ambient room temperature. Because the gas entering the cylinder is at ambient room temperature, differential of the same magnitude will exist between the cylinder and the gas entering it. For example, a 3° C. differential, which may frequently occur during actual use, will introduce approximately 1% error in the displaced gas volume due to expansion in addition to the ±0.5% variations in volume discussed above.

Some embodiments described herein relate to reducing temperature differentials between a syringe cylinder and ambient room air. This can be achieved by increasing the thermal coupling of the cylinder with the room air. For example, as discussed in further detail below with reference to FIG. 4, a syringe having a heat sink that can increase the surface area of the syringe by at least three times, can provide improved thermal coupling of the cylinder with the ambient room air. As further discussed below, in some embodiments, heat sinks can have the additional benefit of minimizing the possible contact surface area if a hand or other portion of an operator's body is placed on the syringe.

Some embodiments described herein relate a syringe that includes a heat sink such that the syringe cylinder has a surface area that is at least three times greater than that of a corresponding smooth cylinder. Some embodiments described herein also relate to moving a piston within a syringe having a heat sink such that the syringe draws a gas mixture into the syringe. The gas mixture can be held within the syringe for at least five seconds, and the heat sink can maintain the temperature of the gas mixture within 1° C. of ambient temperature even if, for example, the syringe is in contact with a body of the operator or exposed to sunlight. The piston can be moved within the syringe such that the gas mixture is expelled from the syringe into a pulmonary function test device. The portion of the gas mixture expelled from the syringe can be within 1° C. of ambient temperature such that the volume per mole (specific volume) of gas mixture is substantially unchanged from when the gas mixture is drawn into the syringe to when the gas mixture is expelled from the syringe.

Some embodiments described herein relate to a method that includes drawing ambient atmospheric gas having a room temperature into a syringe. The syringe can include a housing defining a primary surface area of the syringe, a piston, and a heat transfer element coupled to the housing that has a surface area at least three times greater than the primary surface area of the syringe. The gas can be transferred from the syringe into a PFT device and the PFT device can be validated at least in part on a measurement of a volume of gas transferred between the PFT device and the syringe.

Some embodiments described herein relate to a system and method for performing, validating, and/or calibrating volume measurements using pressurized test gas (such as that used in $D_{LCO}$ test and/or $N_2$ washout lung volumes test using flow-based PFT systems). The syringe can include a compensator that can be a flexible mechanism that presents a fluid dynamic compliance at or near the inlet of the test syringe. The magnitude of the presented compliance may be at least 1 L atm$^{-1}$ which corresponds to the minimum typical physiologic compliance that an adult human would present to the $D_{LCO}$ PFT testing equipment. As described in further detail below with reference to FIGS. 2A-2C, a compensator operates by responding to pressure changes such that the volume it encloses changes proportionally to the pressure changes in that volume. It may be desirable for the compensator to have a high effective bandwidth, because an uncompensated gas delivery device can oscillate at frequencies on the order of 100 Hz. High bandwidth can be accomplished by minimizing the mass of the compensator (e.g., thin construction) and by locating the compensator in close proximity to the syringe inlet, which can reduce inertial and resistive effects of the intervening gas. A viable compensator with a physiologic compliance value can be constructed from silicon or other elastomeric rubber approximately 1 mm thick with a surface area on the order of 32 cm$^2$.

Some embodiments described herein relate to a syringe that includes a syringe body (also referred to as a housing), a piston disposed within the syringe body, and a compliance feature. The compliance feature can be coupled to an outlet portion of the syringe body and can be configured to simulate compliance of a human respiratory system. For example, in some embodiments, the compliance feature can have a compliance greater than 1 L atm$^{-1}$ and/or less than 3 L atm$^{-1}$.

Some embodiments described herein relate to a method that includes coupling a syringe to a pulmonary function test device. The pulmonary function test device can include a demand valve that is configured and/or tuned to supply a test gas to a human subject when the human subject inhales by matching an inhalation pressure with a supply pressure. The demand valve can have a dynamic behavior that is tuned to a human respiratory system. After coupling the syringe to the pulmonary function test device, test gas can be drawn into the syringe, and the compensator can simulate a human respiratory system such that the demand valve operates within its design envelope and such that gas is drawn into the syringe at a substantially constant pressure at or near atmospheric pressure. The test gas can subsequently be expelled from the syringe into the pulmonary function test device.

Some embodiments described herein relate to a method that includes coupling a port of a syringe to a PFT device. The syringe can include a housing, a piston, and a compensator such that the syringe has a fluid dynamic compliance of at least 1 L atm$^{-1}$. Gas can be transferred between the PFT device and the syringe, and the PFT device can be validated based at least in part on a measurement of the gas transferred between the pulmonary function test device and the syringe. For example, the PFT device can include a tank of pressurized gas and a demand valve configured to supply gas from the tank at or near atmospheric pressure to a human subject. The fluid dynamic compliance of the syringe can simulate the fluid dynamic compliance of a human subject such that gas delivered to the syringe via the demand valve is delivered at atmospheric pressure and/or within the design envelope of the demand valve. Thus, the measurement of the gas can be performed on gas delivered to the syringe within the design envelope of the demand valve.

Some embodiments described herein relate to a syringe that includes a piston moveably disposed within a housing. The piston and the housing can collectively define a first working volume when the piston is in a first position and a second working volume when the piston is in a second position. The piston can be configured to discharge, though a port, gas having a volume equal to a difference between the first working volume and the second working volume when the piston is moved from the first position to the second position. The syringe can have a fluid dynamic compliance of at least 1 L atm$^{-1}$.

Some embodiments described herein relate to a system that includes a syringe and a PFT device. The syringe can have a dynamic compliance of at least 1 L atm$^{-1}$. The PFT device can include or be configured to be coupled to a pressurized source of a test gas. The PFT device can be configured to be coupled to the syringe such that the syringe can draw gas from the pressurized source. In some such embodiments, the PFT device can include a demand valve and the syringe can be configured to simulate a human respiratory system such that the demand valve operates within its design envelope when the syringe draws gas from the pressurized source. The PFT device can include a volume sensor configured to measure a volume of gas moving between the PFT device and the syringe and a gas analyzer configured to measure a concentration of test gas expelled into the PFT device from the syringe.

Some embodiments described herein relate to a method that includes filling a syringe with a test gas from a test gas source such that a mixing volume of the syringe contains a first gas mixture having a first concentration of the test gas equal to a concentration of the test gas source. A portion of the first gas mixture can be expelled into a device configured to measure concentrations of the test gas (e.g., a pulmonary function test device). A concentration of the test gas in the first gas mixture can be measured and/or recorded by the device in response to expelling the portion of the first gas mixture into the device. The syringe can be filled with ambient air after expelling the portion of the first gas mixture such that the mixing volume of the syringe contains a second gas mixture having a second concentration of the test gas. A portion of the second gas mixture that has a volume equal to the volume of the portion of first gas mixture can be expelled into the device. A concentration of the test gas in the second gas mixture can be measured and/or recorded by the device in response to expelling the portion of the second gas mixture. The syringe can be filled with ambient air after expelling the portion of the second gas mixture such that the mixing volume of the syringe contains a third gas mixture having a third concentration of test gas. A portion of the third gas mixture having a volume equal to the volume of the portion of the second gas mixture can be expelled into the device. A concentration of the test gas in the third gas mixture can be measured and/or recorded by the device in response to expelling the portion of the third gas mixture into the device. A decay rate coefficient can be determined based on the measured concentration of the test gas in the first gas mixture, the measured concentration of the test gas in the second gas mixture, and the measured concentration of the test gas in the third gas mixture. A correction factor can be determined and/or applied to the device based on the decay rate coefficient. The correction factor can offset at least one of: (i) a deviation between the measured concentration of the test gas in the first gas mixture and the actual concentration of the test gas in the first gas mixture, (ii) a deviation between the measured concentration of the test gas in the second gas mixture and the actual concentration of the test gas in the second gas mixture, or (iii) a deviation between the measured concentration of the test gas in the third gas mixture and the actual concentration of the test gas in the third gas mixture.

Some embodiments described herein relate to a method that includes serially diluting a test gas. Serially diluting a test gas can include expelling a portion of a first gas mixture having a first concentration of a test gas from a mixing volume of a syringe into a device configured to measure concentrations of the test gas (e.g., a pulmonary function test device). A concentration of the test gas in the first gas mixture can be measured and/or recorded by the device in response to expelling the portion of the first gas mixture into the device. The syringe can be filled with ambient air after expelling the portion of the first gas mixture such that the mixing volume of the syringe contains a second gas mixture having a second concentration of the test gas less than the first concentration of the test gas. A portion of the second gas having a volume equal to the volume of the portion of first gas mixture can be expelled into the device. A concentration of the test gas in the second gas mixture can be measured and/or recorded by the device in response to expelling the portion of the second gas mixture into the device. The syringe can be filled with ambient air after expelling the portion of the second gas mixture such that the mixing volume of the syringe contains a third gas mixture having a third concentration of test gas less than the second concentration of test gas. A portion of the third gas mixture having a volume equal to the volume of the portion of the second gas mixture can be expelled into the device. A concentration of the test gas in the third gas mixture can be measured and/or recorded by the device in response to expelling the portion of the third gas mixture into the device. The measured concentration of the test gas in the first gas mixture, the measured concentration of the test gas in the second gas mixture, and the measured concentration of the test gas in the third gas mixture can collectively define a measured decay curve.

The method can further include serially concentrating a test gas. Serially concentrating the test gas can include filling a syringe from a test gas source that the mixing volume of the syringe contains a fourth gas mixture having a fourth concentration of the test gas. A portion of the fourth gas mixture can be expelled into the device. A concentration of the test gas in the fourth mixture can be measured and/or recorded by the device in response to expelling the portion of the fourth gas mixture into the device. The syringe can be filled from the test gas source after expelling the portion of the fourth gas mixture such that the mixing volume of the syringe contains a fifth gas mixture having a fifth concentration of the test gas greater than the fourth concentration of the test gas. A portion of the fifth gas mixture having a volume equal to a volume of the portion of the fourth gas mixture can be expelled into the device. A concentration of the test gas in the fifth gas mixture can be measured and/or recorded by the device in response to expelling the portion of the fifth gas mixture into the device. The syringe can be filled with test gas from the test gas source after expelling the portion of the fifth gas mixture such that the mixing volume of the syringe contains a sixth gas mixture having a sixth concentration of the test gas greater than the fifth concentration of the test gas. A portion of the sixth gas mixture having a volume equal to the volume of the portion of the fifth gas mixture can be expelled into the device. A concentration of the test gas in the sixth gas mixture can be measured and/or recorded by the device in response to expelling the portion of the sixth gas mixture into the device. The measured concentration of the test gas in the fourth gas mixture, the measured concentration of the test gas in the fifth gas mixture, and the measured concentration of the test gas in the sixth gas mixture collectively defining a measured growth curve.

The method can further include simultaneously characterizing (i) a linearity of the device, (ii) a dilution mixing ratio defined by the mixing volume and the volume of the portion of the first gas mixture, and (iii) a growth mixing ratio defined by the mixing volume and the volume of the portion of the fourth gas mixture. The device can be validated and/or calibrated based on the linearity of the device such that, when a seventh gas mixture is expelled into the device, the device reports a concentration of test gas in the seventh gas mixture consistent with an actual concentration of test gas within the seventh gas mixture.

Some embodiments described herein relate to a method that includes fluidically coupling a syringe that is in a maximum volume configuration to a PFT device. The syringe can be moved from the maximum volume configuration to a minimum volume configuration while the syringe is fluidically coupled to the pulmonary function test device such that a first gas mixture is expelled from the syringe into the PFT device. A concentration of the test gas in the first gas mixture can be measured using a gas analyzer. The syringe can be moved from the minimum volume configuration to the maximum volume configuration while the syringe is fluidically coupled to the pulmonary function test device such that the syringe draws a displacement volume of the test gas from the pulmonary function test device and such that the displacement volume less a system volume of the test gas mixes with a dead-space volume of the first gas mixture in the syringe to create a second gas mixture. The syringe can be moved from the maximum volume configuration to the minimum volume configuration while the syringe is fluidically coupled to the pulmonary function test device such that the second gas mixture is expelled from the syringe into the PFT device. The concentration of the test gas in the second gas mixture can be analyzed. The method can include performing any number of serial concentrations by mixing test gas with a previous mixture of gas remaining in the dead-space of the syringe and/or measuring the concentration of the test gas in any of the serial concentrations. As described in further detail herein, the mixing ratio of the syringe and the distortion function of the PFT device/gas analyzer can be simultaneously determined based on the measured concentrations of test gas. The PFT device/gas analyzer can be validated and/or calibrated based on the mixing ratio of the syringe and the distortion function of the PFT device/gas analyzer.

Some embodiments described herein relate to a method that includes determining, based on a first signal received from a gas analyzer, a first measured concentration of a test gas contained within a first gas mixture injected into a PFT device from a syringe that has a first mixing ratio. A second measured concentration of the test gas contained within a second gas mixture that includes a portion of the first gas mixture diluted with atmospheric gas according the first mixing ratio can be determined based on a second signal received from the gas analyzer. A third measured concentration of the test gas contained within a third gas mixture that includes a portion of the second gas mixture diluted with atmospheric gas according the first mixing ratio can be determined based on a third signal received from the gas analyzer. A measured decay rate can be determined based on the first measured concentration of the test gas, the second measured concentration of the test gas, and the third measured concentration of the test gas, and an eigenfunction over the measured decay rate can be defined. A fourth measured concentration of the test gas contained within a fourth gas mixture injected into a PFT device from the syringe can be measured based on a fourth signal received from the gas analyzer. A fifth measured concentration of the test gas contained within a fifth gas mixture that includes a portion of the fourth gas mixture concentrated with the test gas according to a second mixing ratio can be determined based on a fifth signal received from the gas analyzer. A sixth measured concentration of the test gas contained within a sixth gas mixture that includes a portion of the fifth gas mixture concentrated with the test gas according to a second mixing ratio can be determined based on a sixth signal received from the gas analyzer. A measured concentration rate based on the fourth measured concentration of the test gas, the fifth measured concentration of the test gas, and the sixth measured concentration of the test gas can be determined, and an eigenfunction over the measured concentration rate can be defined. The eigenfunction over the measured decay rate and the eigenfunction over the measured concentration rate can be simultaneously solved to simultaneously determine the first mixing ratio, the second mixing ratio, and a set of coefficients representing the non-linearity of the gas analyzer.

FIGS. 1A-1D depict schematic illustrations of syringe 100 in various configurations and a PFT device 200, according to an embodiment. The PFT device 200 includes a gas analyzer 210, a volume sensor 220, a processor 212, and memory 214. The syringe 100 is configured to draw and expel gas through the PFT device 200. Similarly stated, the syringe 100 is fluidically coupled to the PFT device 200.

The PFT device 200 includes an exhaust valve 232 and an intake valve 234. In some embodiments, each of the exhaust valve 232 and the intake valve 234 is or can be configured to be a one-way valve. The PFT device can be connected to a supply of test gas 236 via the intake valve 234. The supply of test gas 236 can be a pure test gas (e.g., carbon monoxide, methane, etc.) suitable for detection by the gas analyzer 210 or a gas mixture containing the test gas. As described in further detail herein, the concentration of the test gas in the supply of test gas 236 may be unknown and/or the supply of test gas 236 can have an arbitrary concentration.

The processor 212 and/or the memory 214 can be communicatively coupled to the gas analyzer 210 and/or the volume sensor 220 and operable to process signals received from the gas analyzer 210 and/or the volume sensor 220 and send and/or store a signal representing a concentration of gas and/or measured volume. Similarly stated, the processor 212 and/or the memory 214 can be operable to process raw signals from the gas analyzer 210 and/or the volume sensor 220 (or any other suitable sensors) and produce a calculated value. For example, the processor 212 can be operable to integrate a signal associated with a linear and/or volumetric flow rate from the volume sensor 220 to produce a measurement of volume. In some embodiments, the memory 214 can contain models, correlation coefficients, and/or other instructions that, when executed by the processor 212, cause the processor to calculate, report, and/or store a measured value. Some embodiments described herein relate to calibrating a PFT device. Calibrating a PFT device can include altering models, calibration coefficients, and/or the like, stored in the memory 214. Thus, some embodiments relate to altering or producing a PFT device using the devices and methods described herein having calibration coefficients, models, or other suitable information stored in memory such that the PFT device performance is improved. In a clinical environment, a PFT device calibrated using the methods and/or apparatus described herein may be operable to measure volume, gas concentration, and/or physiologic parameters more accurately and/or with more precision than current existing PFT devices that have not been calibrated using the devices and/or methods described herein.

FIG. 1A shows the syringe 100 in a first configuration in which the PFT device 200 and the syringe include ambient gas (e.g., atmosphere). For example, the configuration shown in FIG. 1A can be the result from the PFT device 200 being flushed with ambient gas, for example, by the syringe 100.

The syringe 100 includes a diffusion barrier 110, a piston 120, a first stop 130, and a second stop 140. The first stop 130 can be configured to define a maximum volume of the syringe 100, while the second stop 140 can be configured to define a minimum volume of the syringe 100. In some embodiments, the first stop 130 and/or the second stop 140 can be moveable, such that the maximum and/or minimum volumes of the syringe 100 are adjustable. As shown in FIG. 1A, the second stop 140 is disposed against a back portion 150 of the syringe 100 such that the syringe 100 is in a minimum-volume configuration. In the minimum-volume configuration, a dead space volume $V_{dead}$ of the syringe 100 is defined.

FIGS. 1B and 1C show the syringe 100 in a second configuration in which the first stop 130 is disposed against the back portion 150 of the syringe 100 such that the syringe 100 is in a maximum-volume configuration. The piston 120 can be moved from the first configuration shown in FIG. 1A to the second configuration shown in FIGS. 1B and 1C by drawing it towards the back portion 150 of the syringe 100. Drawing the piston 120 such that it moves towards the second configuration causes gas to be drawn from the supply of test gas 236 through the intake valve 234 and the PFT device 200 and the diffusion barrier 110 into the syringe 100. The diffusion barrier 110 allows gas flow when the piston 120 is moving, but inhibits gas diffusion when the piston 120 is stationary. Thus, the PFT device 200 can be filled with gas from the supply of test gas 236, and the diffusion barrier 110 inhibits gas from entering or leaving the syringe 100 when the piston 120 is stationary.

The volume of gas drawn into the syringe 100 through the displacement of the piston 120 is referred to herein as the displaced volume $V_i$ (also referred to as the inspired volume). The sum of the displaced volume $V_i$ and the dead space volume $V_{dead}$ is the mixing volume $V_{mix}$ of the syringe 100. The volume of a gas channel of PFT device 200 and/or any volume between the intake valve 234 and the diffusion barrier 110 is a system volume $V_{system}$. FIG. 1B schematically depicts the various volumes separately. FIG. 1C depicts a mixture of the displaced volume $V_i$ and the dead space volume $V_{dead}$ in which the gas from the supply of the test gas 236 is diluted by ambient air from the dead space volume $V_{dead}$ and system volume $V_{system}$.

FIG. 1D shows the syringe 100 in a third configuration in which the second stop 140 is disposed against the back portion 150 of the syringe 100 such that the syringe 100 is in a minimum-volume configuration. The piston 120 can be moved from the second configuration shown in FIGS. 1B and 1C to the third configuration shown in FIG. 1D by pushing it away from the back portion 150 of the syringe 100. Pushing the piston 120 such that the syringe 100 moves towards the third configuration causes the gas within the PFT device 200 to be expelled via the exhaust valve 232 and the mixture of ambient air and gas from the supply of test gas 236 shown in FIG. 1C to fill the PFT device 200. As described in further detail herein, the piston 120 can be reciprocated any number of times. Each time the piston 120 moves towards the back portion 150 of the syringe, the concentration of test gas in the syringe can increase.

The syringe 100 has a diluting behavior described by $$A = \frac{V_i - V_{system}}{V_{mix}} \quad (1)$$

$$M_k = AM_{src}(1-A)M_{k-1} \quad (2)$$

Where,
A is the mixing ratio of the syringe,
$V_i$ is the displacement volume, shown and described above with reference to FIG. 1B,
$V_{system}$ is the system volume, shown and described above with reference to FIG. 1B,
$V_{mix}$ is the mixing volume, shown and described above with reference to FIG. 1B,
$M_k$ is the diluted, mixed concentration of the test gas in the mixing volume $V_{mix}$,
$M_{src}$ is the concentration of the test gas in the test gas source 236, and
$M_{k-1}$ is the concentration of the test gas in the dead volume $V_{dead}$ and system volume $V_{system}$ prior to drawing gas from the test gas source 236, shown and described above with reference to FIG. 1D.

FIG. 2A is a schematic illustration of a syringe 300 and a PFT device 400, according to an embodiment. The syringe 300 and the PFT device 400 can be structurally and/or functionally similar to the syringe 100 and the PFT device 200 as shown and described above with reference to FIGS. 1A-D. The syringe 300 includes a piston 320 operable to cause the syringe 300 to draw gas from a test gas source 436 via the PFT device 400 and an intake valve 434. The syringe 300 can be operable to draw gas to/from the PFT device 400, and the PFT device 200 (e.g., the volume sensor 210 and/or a gas analyzer 220) can be validated based at least in part on a measurement of gas transferred between the PFT device 400 and the syringe 300.

The test gas source 436 can be a pressurized gas source (e.g., a tank and/or a connection to a high-pressure test gas line) and the intake valve 434 can be or include a demand valve and/or regulator operable to regulate the pressure of the test gas such that the PFT device 400 receives the test gas at or near atmospheric pressure. The demand valve can be configured to supply the test gas mixture when the human subject inhales at atmospheric pressure by dynamically matching the pressure at which the test gas mixture is supplied to the inhalation pressure.

The intake valves (e.g., demand valves) of known PFT devices are typically designed to supply gas based on the inhalation of a human subject. Such intake valves may be conditionally stable, that is, they are stable only within a finite envelope of operating conditions. One important parameter of that envelope is the dynamic characteristic of the "load" to which the regulator delivers gas. The "load" in this case is a human being tested, which presents a fairly large dynamic compliance to the regulator. In an adult human, the extra-thoracic structure of the airways (e.g., mouth, nasal and larynx) is flexible and presents a dynamic compliance in the range of 1-3 L atm$^{-1}$.

Existing devices used to validate and/or calibrate PFT equipment are typically not operable to provide a dynamic load to the intake valves that is similar to a human being. For example, existing dilution syringes and the like typically have a compliance less than approximately one-tenth the compliance of a human being and therefore, if fluidically coupled to a PFT device, the intake valve may operate outside its design envelope resulting in deviations from expected and/or designed gas delivery behavior. For example, gas may be delivered from the test gas source 436 at a higher or lower pressure than atmospheric or the delivered pressure may oscillate with a large amplitude, potentially disrupting any flow measurements.

The syringe 300 includes a compliance feature 330. The compliance feature 330 can be an elastic structure such that the syringe 300 has a compliance similar to a human upper-respiratory system and such that the syringe 300 presents a dynamic load to the PFT equipment 400 similar to a human being. Similarly stated, the syringe 300 including the compliance feature 330 can have a dynamic compliance between 1 and 3 L atm$^1$. In this way, the intake valve 434 can operate within its design envelope and gas can be delivered from the test gas source 436 at or near (e.g., within 5%) atmospheric pressure. Thus, the volume and/or concentration of the gas drawn from the gas source 436 into the syringe 300 can be well characterized and suitable for use validating and/or calibrating the PFT device 400 for test modalities such as an $N_2$ washout lung volumes test and/or a $D_{LCO}$ test.

In some embodiments, the compliance feature 330 can include a conduit for gas partially and/or completely constructed of an elastomeric material, such as silicon rubber or the like. In some embodiments, the compliance feature can be constructed of silicon rubber having a thickness between 0.25 mm and 4 mm and a surface area between 13 cm$^2$ and 52 cm$^2$ (e.g., 1 mm thick and surface area of 32 cm$^2$). For example, the compliance feature 330 can be a cylindrical and/or other suitable hollow body and/or passageway defining openings to atmosphere that are covered by an elastomeric material. Similarly stated, the openings would be open to atmosphere but for the elastomeric covering. The compliance feature 330 can be disposed on an end portion of the syringe 300 that is configured to be coupled to the PFT device 400 (e.g., opposite the piston), which can reduce inertial effects of gas within the syringe 300 that can reduce the effectiveness of compliance feature 330.

In addition or alternatively, the compliance feature 330 can be an elastomeric bellows-like structure, such as a structure that includes accordion folds. Alternatively, the compliance feature 330 can be a servomechanism or other suitable electro-mechanical device coupled to the piston 320 and configured to move the piston in response to changes in pressure to generate the fluid dynamic compliance.

The compliance feature 330 operates by responding to pressure changes such that the volume enclosed by the compliance feature changes proportionally to pressure changes in that volume. The compliance feature 330 can have a bandwidth suitable to simulate a human respiratory system to various demand valves and similar feedback control mechanisms. Some existing demand valves can oscillate at frequencies on the order of 100 Hz. Thus, the compliance feature 330 can be operable to simulate a human respiratory system and/or dynamically stabilize a demand valve at frequencies of 100 Hz and higher. In some embodiments, the use of thin and/or low density materials for the construction of the compliance feature 330 (e.g., a thin film) can provide a suitably low-mass compliance feature 330 with a sufficiently high bandwidth to simulate the human respiratory system.

Figure 2B:
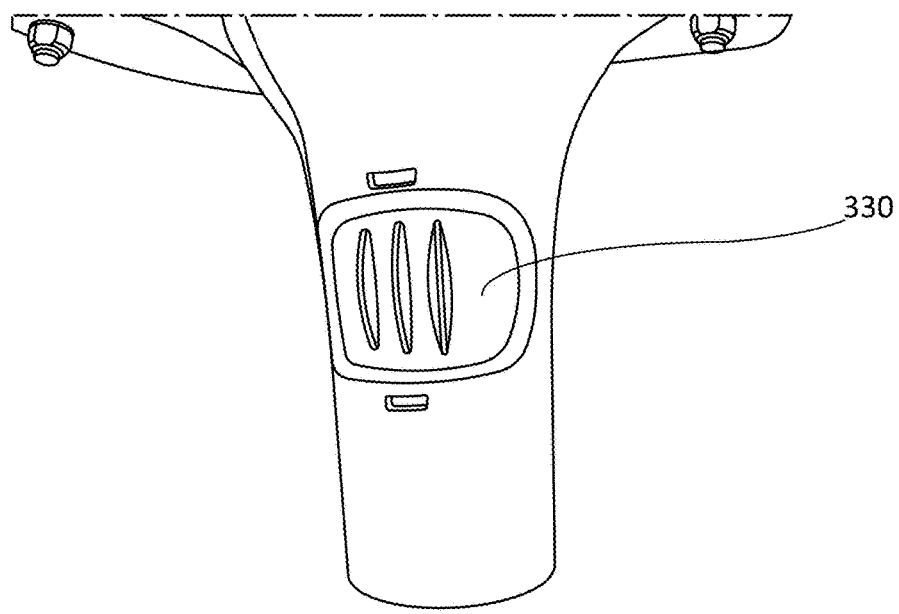
FIGS. 2B-2C are close-up illustrations of a compliance feature of a syringe.
Figure 2C:
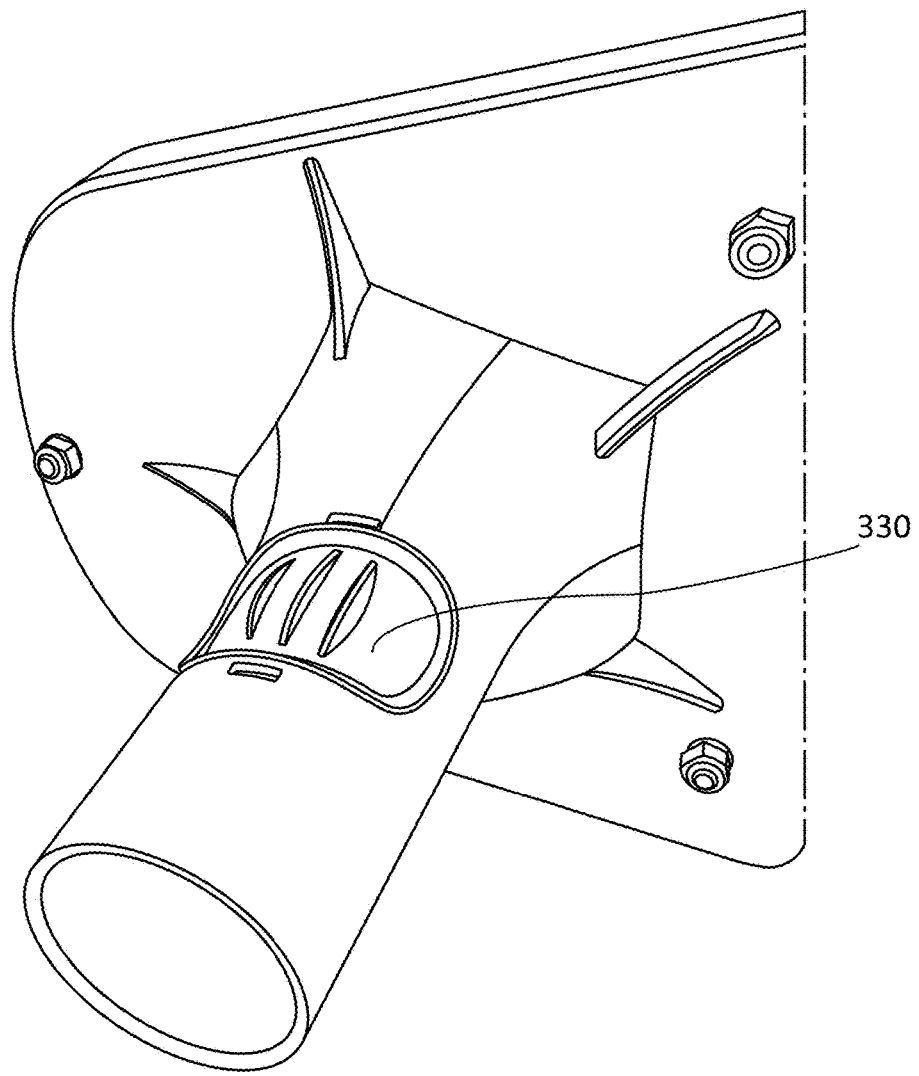

An exemplary compliance feature 330 is shown in more detail in FIGS. 2B and 2C. As shown in FIGS. 2B and 2C, the compliance feature 330 is a bellows-like structure constructed of silicon rubber and disposed on an end portion of a syringe.

Figure 3A:
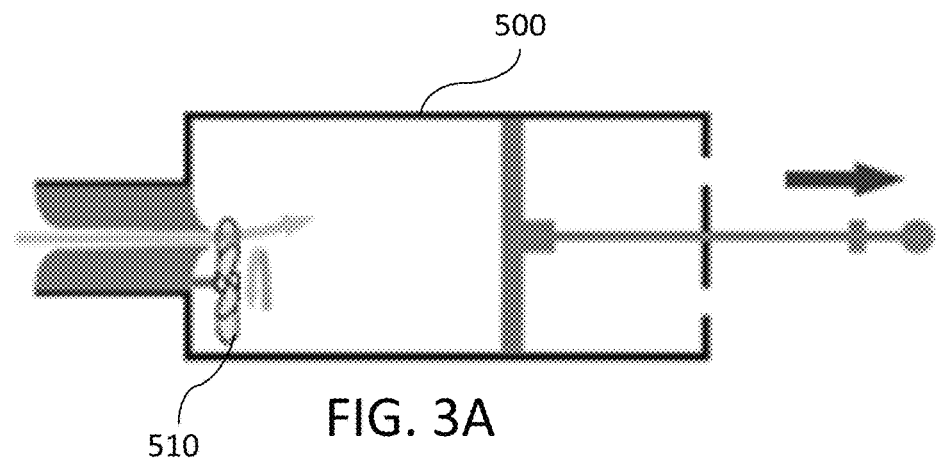
FIG. 3A is a schematic illustration of a syringe having a passive mixing feature, according to an embodiment.

FIG. 3A is a schematic illustration of a syringe 500 having a passive mixing feature 510 (also referred to herein as a fan or agitator), according to an embodiment. The syringe 500 can be structurally and/or functionally similar to the syringes 100 and/or 300 discussed above. In particular, the syringe 500 can be operable to calibrate and/or validate PFT equipment having a gas analyzer (not shown in FIG. 3). The syringe 500 can be a dilution syringe operable to mix gas from a test gas source with atmosphere or previous mixture. The passive mixing feature 510 can reduce wait times and/or improve mixing characteristics of the syringe 500. In some embodiments the mixing feature 510 can be an undriven fan operable to be mechanically energized by gas flowing into and/or out of the syringe. Similarly stated, the mixing feature can be operable to freely spin or pinwheel when gas is drawn into the syringe. In some embodiments a nozzle or similar structure can cause relatively high velocity gas to impinge upon the mixing feature 510. In other embodiments, the mixing feature 510 can be operable to agitate gases within the syringe 500 by any other suitable means, such as vibrational agitation, creating vortices or other suitable turbulent flow patterns within the syringe 500 and/or so forth. In some embodiments, the mixing feature 510 can continue to agitate gas within the syringe 500 after the piston has come to rest, for example, through inertial effects. A passive mixing feature can be preferable to an active mixing feature and/or driven fan for simplicity of construction and to avoid heating the gas within the syringe, which as described in further detail herein can produce inaccuracies when calibrating and/or validating a gas and/or volume sensor of a PFT device.

In some instances, the syringe 500 can be operable to simulate a Jones-Mead, single-breath $D_{LCO}$ test. In a Jones-Mead, single-breath $D_{LCO}$ test, the subject inhales a test gas, holds his or her breath for approximately 10 seconds and then exhales. The passive mixing feature 510 can be operable to cause an inspired test gas (e.g., $V_i$) to completely mix with a dead volume of gas (e.g., $V_{dead}$) within 10 seconds or less.

Figure 3B:
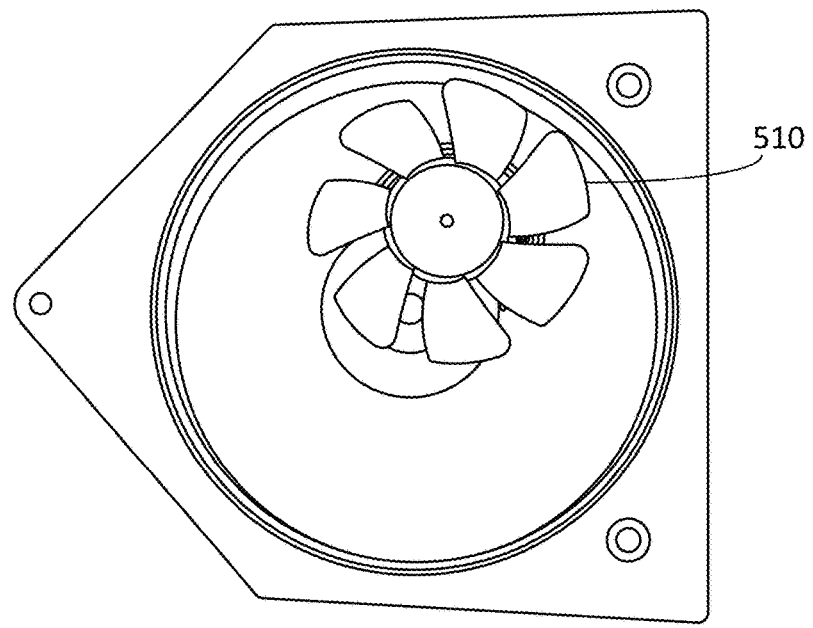
FIGS. 3B-3C are close-up illustrations of a passive mixing feature.
Figure 3C:
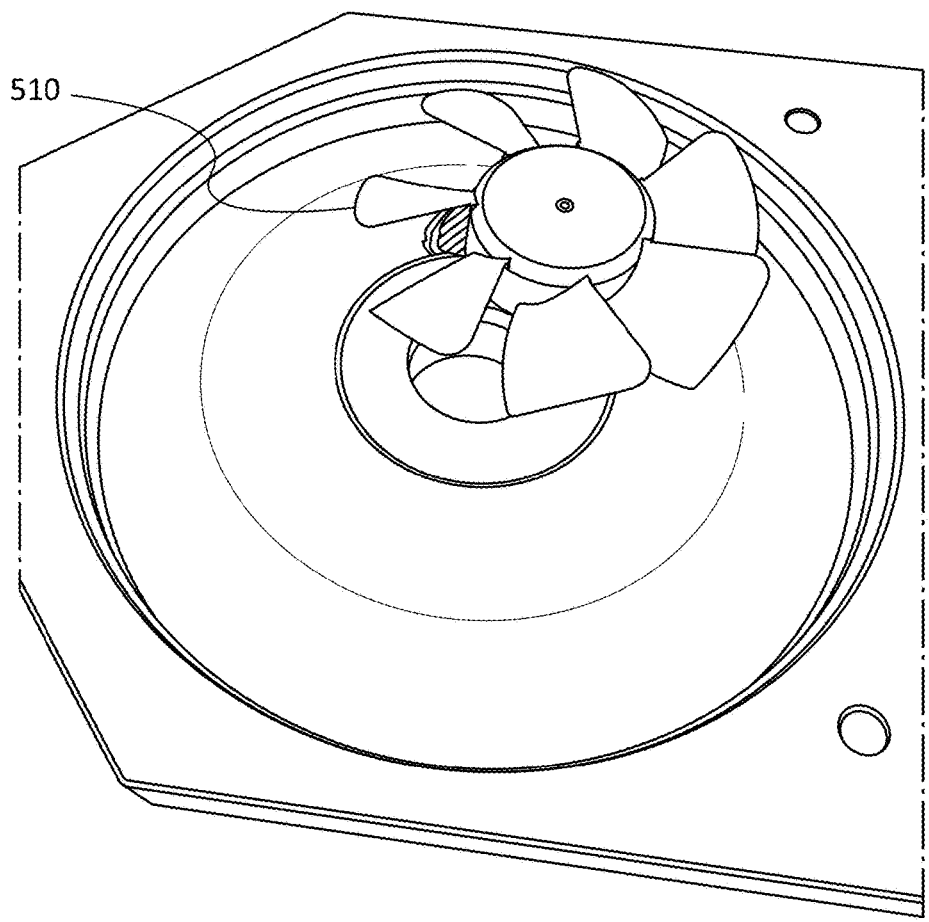

An exemplary mixing feature 510 is show in more detail in FIGS. 3B and 3C.

Figure 4:
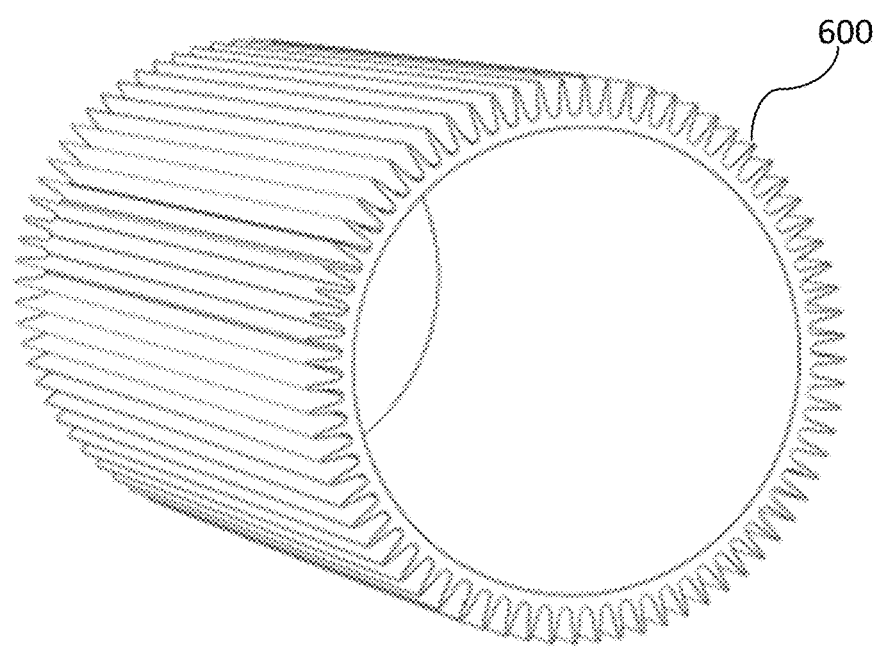
FIG. 4 is an illustration of an embodiment of a heat sink for a syringe.

FIG. 4 is an illustration of an embodiment of a heat sink 600 for a syringe, such as the syringes 100, 300, and/or 500 as described above. Existing devices and methods for validating and/or calibrating volume sensors of PFT devices (e.g., spirometers and the like) typically involve injecting a standard volume of gas from a syringe. To calibrate and/or validate a PFT device with sufficient accuracy to provide physiological representative and/or clinically meaningful data, syringes are typically accurate to ±0.5% of their mechanical displaced volume. Relatively large 3 L or 7 L syringes are common.

In use, an operator holds the syringe and reciprocates the plunger. Because of the size and weight of such syringes, it is common for the operator to place a hand on the syringe body or cradle the syringe in his or her arms. Such contact with the operator can cause the temperature of the cylinder to rise appreciably above the ambient air, causing the temperature of any gas that enters the cylinder to also rise appreciably above ambient. A rise of the internal gas temperature of as little as 3° C. can introduce volumetric errors of 1% or greater, resulting in an inability to calibrate and/or validate a PFT device to manufacturer specifications and/or clinical standards.

The heat sink 600 can increase the thermal conductivity between the ambient atmosphere and the syringe cylinder, keeping the cylinder's temperature closer to the temperature of the ambient air, which may vary due to exposure to HVAC and related variables, or when the cylinder is exposed to external heat sources such as the user or direct sunlight. The heat sink 600 will also decrease thermal conductivity between the user and the syringe cylinder by reducing available surface area that the user may contact, thus reducing the amount of heat the user can transfer to the cylinder during normal use. For example, the syringe can be placed in thermal contact with a surface (e.g., a human body at 37° C.) at least 10° C. above room temperature (e.g., 23° C.) an elapsed time of at least two minutes between drawing gas into the syringe and injecting gas into a PFT device. During the elapsed two minutes, the specific volume of gas within the syringe can change by less than 0.2%. In addition or alternatively, during the elapsed two minutes, the temperature within the gas can change by less than 1° C. during the elapsed two minutes.

For example, the heat sink 600 can increase the surface area of the exterior wall of the syringe (also referred to herein as a primary surface area) by at least three times. The heat sink 600 can thereby increase the surface area of the syringe in contact with the atmosphere and the thin fins, as shown, can decrease the surface area available for contact with the user. For example, a syringe can be characterized by its diameter d and length l, such that the surface area of the body of the syringe is π×d×l, excluding the end portions. With the heat sink 600, the surface area of the body of the syringe can be at least three times π×d×l.

Such a syringe can be suitable for validating and/or calibrating a PFT device. For example, a syringe with the heat sink 600 can maintain a temperature of gas within the syringe within 1° C. of ambient when the syringe is in close contact with a body of an operator for 10 seconds or more. Similarly stated, even after being in contact with a body of an operator for 10 seconds or more, the volume per mole of gas within the syringe may remain substantially constant. Thus, the gas within the syringe can be suitable for calibrating and/or validating a spirometer or other suitable volume sensor of a PFT device.

Figure 5:
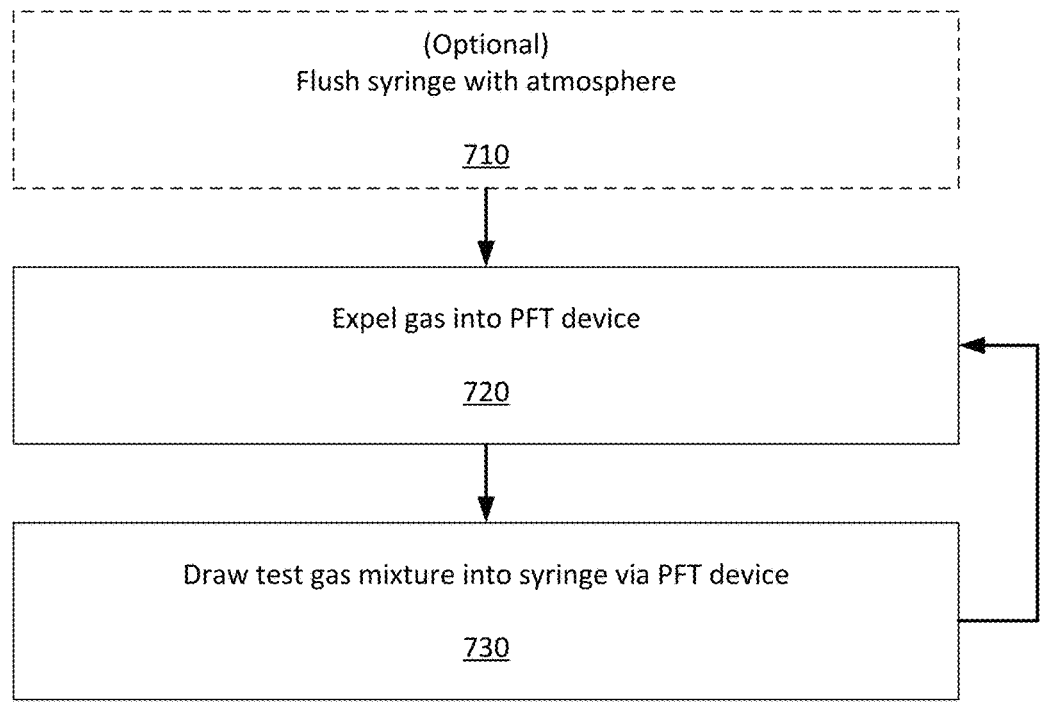
FIG. 5 is a flow chart of a method of calibrating and/or validating a PFT device with a syringe, according to an embodiment.

FIG. 5 is a flow chart of an embodiment of a method of calibrating and/or validating a PFT device with a syringe, such as the syringes 100, 300, and/or 500 as shown and described above. For ease of reference, FIG. 5 is described with reference to FIGS. 1A-D. Optionally, at 710, the syringe 100 can be flushed and/or purged with ambient air such that the syringe 110 includes at most trace amounts of test gas. For example, the syringe 100 can be decoupled from the PFT device 200 and the piston reciprocated a large number of times such that substantially no test gas is within the interior volume of the syringe. The piston of the syringe 100 can then be drawn back such that the syringe is in a maximum-volume configuration and the syringe coupled to the PFT device 200.

At 720, the piston 120 can be moved into a minimum-volume configuration, such as shown in FIG. 1A. In an instance where the syringe 100 was previously flushed with atmosphere, the PFT device 200 can be filled with atmosphere (e.g., as shown in FIG. 1A). The gas analyzer 210 can measure a concentration of test gas in the atmosphere. In some instances the test gas is present only in trace amounts (e.g., 2,500 ppb or less) in the atmosphere and/or the concentration of the test gas in the atmosphere can be below a detection limit of the gas analyzer, such that the gas analyzer 210 reports (or is configured to report) zero test gas.

At 730, the piston 120 can be moved from a minimum-volume configuration, into the maximum-volume configuration. The piston can draw the displaced volume $V_i$ of the test gas mixture from the test gas source 236 through the PFT device 200 and into the syringe. The quantity of the test gas mixture drawn into the syringe (the displacement volume $V_i$ less the system volume $V_{system}$) can mix with the gas disposed within the dead volume $V_{dead}$ and system volume $V_{system}$, as shown, for example, in FIGS. 1B and 1C.

After the piston 120 is moved into the maximum-volume configuration, at 730, the process can be repeated any number of times. Each time the syringe moves into the minimum-volume configuration, at 720, a mixture of test gas and atmosphere can be injected into the PFT device 200, and the concentration of test gas can be measured by the gas analyzer 210. Then, each time the syringe moves into the maximum-volume configuration, at 730, gas drawn from the test gas source 236 can mix with the gas in the dead volume $V_{dead}$ and system volume $V_{system}$ from the previous minimum-volume configuration.

Figure 6:
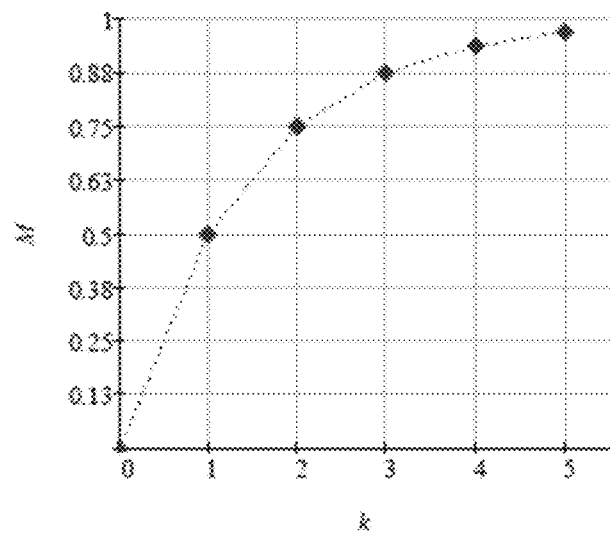
FIG. 6 is a plot of concentrations produced by a syringe operated according to the method of FIG. 5, according to an embodiment.

For example, as shown in FIG. 1D, the piston 120 is moved into the minimum-volume configuration, expelling a mixture of atmosphere and the test gas mixture into the PFT device 200. A concentration of test gas in this mixture can be detected by the gas analyzer 210. Subsequently, the mixture shown in FIG. 1D can be mixed with additional test gas mixture, further concentrating the gas mixture shown in FIG. 1D. This mixture can be expelled into the PFT device 200 and concentration of the test gas in this mixture can again be measured by the gas analyzer 210. In this way, a series of serial concentrations of the test gas can be measured. FIG. 6 is a plot of concentration produced by a syringe operated according to the method of FIG. 5, in an embodiment in which the test gas source 236 contains pure test gas, the atmosphere contains no test gas, and the mixing ratio A is 0.5. As shown in FIG. 6 the concentration of test gas in the syringe approaches the concentration of the test gas mixture asymptotically according to the following formula.

$$M_k = M_{src}(1-A^k) \tag{3}$$

Where,

A is the mixing ratio of the syringe,

M is a concentration of test gas and $M_{src}$ is a concentration of test gas in the test gas source, and k is a cycle index such that $M_k$ is the diluted, mixed concentration of the test gas in the mixing volume $V_{mix}$ after k cycles of the piston.

Gas analyzers used in most commercially available PFT devices typically rely on optical absorption using, for example, non-dispersive infrared (NDIR) analyzers, to measure test gas concentration. According to the Beer-Lambert law, absorption has a linear relationship with gas concentration. NDIR analyzers, however, measure optical absorbance indirectly, relying on the effect that absorption has on detected light intensity and are therefore fundamentally nonlinear. The relationship between absorption and the intensity of light entering and leaving the analyzer's sample chamber is:

$$I_m = I_0 e^{-A} \tag{4}$$

Where,

A is the absorbance, $I_0$ is the light intensity entering the sample chamber, and $I_m$ is the light intensity leaving the chamber.

In addition, practical NDIR implementations introduce additional second order nonlinear behaviors beyond those expressed in equation (4). Furthermore, sensor nonlinearity varies significantly from device to device due to production variability. Accordingly, to provide useful data, a gas analyzer must be calibrated and/or validated. Data generated from gas analyzers (e.g., NDIR analyzers) may also be post-processed and/or linearized to produce a linear representation of the measured gas concentration. Coefficients associated with the linearization process can be obtained by calibrating the analyzer using multiple concentrations of one or more test gases. As discussed above, to validate and/or calibrate a PFT device to manufacturer specifications/clinical requirements and/or to provide physiologically representative/clinically meaningful data, it is desirable for the nonlinearity of gas analyzers to be on the order of 0.5% relative to full scale. Bottled gas references with sufficiently accurate concentrations and range to characterize an analyzer to the accuracy levels required by manufacturer and/or clinical standards are not readily available and/or are extremely expensive. Even if suitable bottled gas mixtures can be created, such standard mixtures are generally unsuitable and/or unavailable for use in the field (e.g., outside the equipment maker's manufacturing facilities).

As a result, rather than using multiple bottled gas references, various dilutions and/or concentrations of a single mixture of test gas can be made using a syringe or similar device, such as the syringes 100, 300, 500 described above. If the nonlinearity of gas analyzers less than ±0.76% relative to full scale is to be verified with a 95% probability, the combined standard deviation of the dilution syringe and the analyzer being verified should be less than 0.38% relative to full scale. This implies that the dilution syringe should generate gas concentration ratio values with a standard deviation on the order of 0.1% relative to full scale, which can be difficult or impossible to achieve by using commercially available gas mixtures.

Some embodiments described herein relate to linearizing, calibrating and/or validating a gas analyzer ratiometrically, rather than relying upon the accuracy of individual gas mixture concentrations. Similarly stated, because existing gas mixing and/or dilution techniques are generally unsuitable for providing a known concentration of a test gas with sufficient accuracy, some embodiments described herein relate to a syringe that, rather than providing highly accurate mixing volumes, produces highly precise and highly repeatable mixing volumes. For example, although the absolute mixing volumes of the syringe shown in FIGS. 1A-1D may not be known with a high degree of accuracy, when the syringe is cycled according to the method described with reference to FIG. 5, each movement of the piston replicates the same volume with a high degree of precision. Accordingly, the syringe will concentrate the test gas according to equation (3) with little deviation (e.g., less than 0.1% deviation from full scale).

Figure 7:
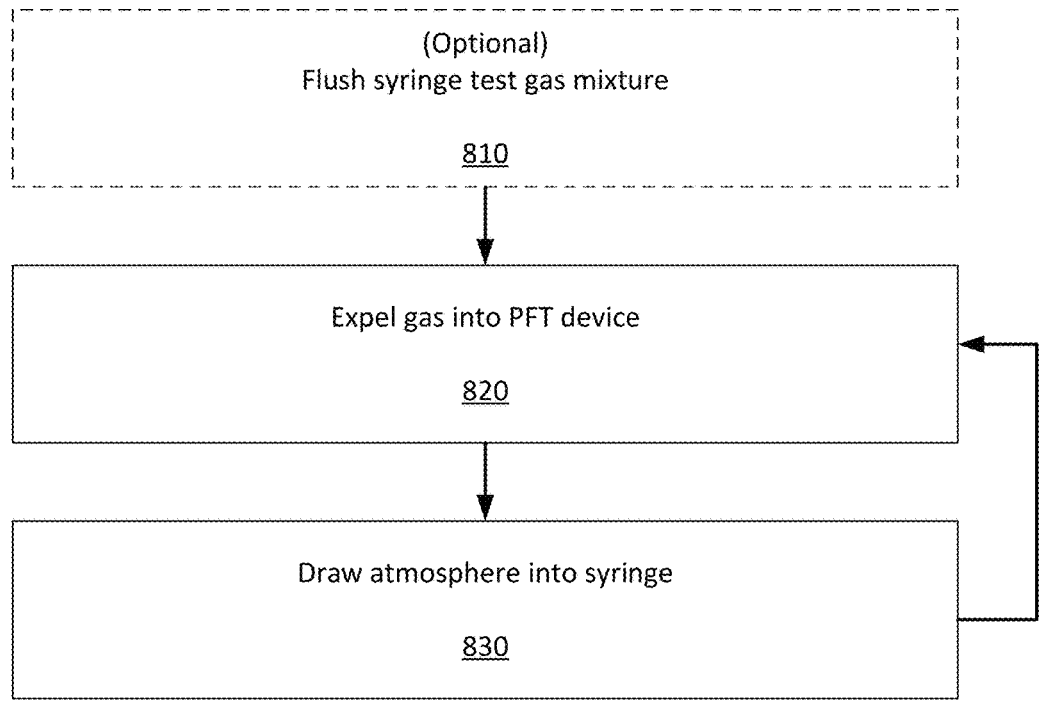
FIG. 7 is a flow chart of a method of calibrating and/or validating a PFT device with a syringe, according to an embodiment.

FIG. 7 is a flow chart illustrating details of simultaneously calibrating and/or validating a syringe and a gas analyzer, according to an embodiment. As discussed above, current art with respect to calibrating or validating a gas analyzer rely on applying a standard with an accurately known concentration of a test gas. As also discussed above, it can be difficult or impossible to produce sufficiently accurate mixtures of the test gas. Rather than apply a standard gas mixture to the gas analyzer, the method of FIG. 7 simultaneously validates and/or calibrates the syringe and the gas analyzer, without relying on a standard concentration of test gas. The method of FIG. 7 is partially an exponential complement of the method shown and described with reference to FIGS. 5 and 6. FIGS. 5 and 6 describe an exponential serial concentration of test gas using a syringe. FIG. 7 describes an exponential serial dilution of test gas.

At 810, optionally, the syringe 100 can be flushed and/or purged with gas from test gas source 236 such that the syringe 100 includes at most trace amounts of atmospheric gas. For example, the state of the syringe at 810 can be achieved by performing the method of FIG. 5 a large number of times such that the mixing volume $V_{mix}$ of the syringe includes a mixture of gas having a concentration of test gas approaching the concentration of test gas in the test gas source 236.

At 820, the syringe 100 can be moved into a minimum-volume configuration expelling the displaced volume $V_i$ into the PFT device 200, and the gas analyzer 210 can measure a concentration of test gas in the mixture. Then, at 830, the syringe 100 can be moved from a minimum-volume configuration, into the maximum-volume configuration. The piston 120 can draw the displaced volume $V_i$ of the atmosphere into the syringe 100. For example, the test gas source 236 can be decoupled from the PFT device, the intake valve 234 can be moved into a configuration in which it draws atmosphere rather than gas from the test gas source, and/or the exhaust valve 232 can be reversed such that it functions as an intake valve. The quantity of the atmosphere drawn into the syringe 100 (the displacement volume $V_i$ less the system volume $V_{system}$) can mix with the gas disposed within the dead volume $V_{dead}$ and system volume $V_{system}$.

After the syringe 100 is moved into the maximum-volume configuration, at 830, the process can be repeated any number of times. Each time the syringe 100 moves into the minimum-volume configuration, at 820, a mixture of test gas and atmosphere can be injected into the PFT device 200, and the concentration of test gas can be measured. Then, each time the syringe moves into the maximum-volume configuration, at 830, atmosphere can be drawn into the syringe and mix with the gas remaining in the dead volume $V_{dead}$ and system volume $V_{system}$ from the previous minimum-volume configuration. In this way a series of serial dilutions of the test gas can be measured.

Figure 8:
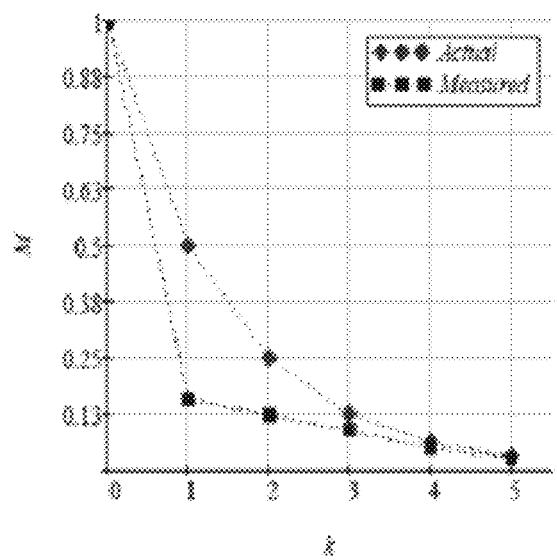
FIG. 8 is a plot of actual and measured concentrations produced by a syringe operated according to the method of FIG. 7, according to an embodiment.

FIG. 8 is a plot showing the theoretical actual concentration of test gas delivered by a syringe operated according to the method of FIG. 7, in an embodiment in which the syringe is initially flushed with 100% test gas, the atmosphere contains no test gas, and the mixing ratio A is 0.5. FIG. 8 further shows a simulation of a measured concentration of the concentration of the test gas according to a PFT device. As shown in FIG. 8 the concentration of test gas in the syringe approaches zero (or more accurately, the concentration of test gas in the atmosphere) asymptotically according to the following formula.

$$M_k = M_{src} A^k \qquad (5)$$

Where,

A is the mixing ratio of the syringe,

M is a concentration of test gas and $M_{src}$ is a concentration of test gas in the test gas source, and k is an cycle index such that $M_k$ is a the concentration of the test gas in the mixing volume $V_{mix}$ after k cycles of the piston.

Notably, equation (5) (and equation (3) described above) are independent of any individual measurement of the concentration of the test gas and of all parameters of the dilution syringe other than mixing ratio A. Methods described herein effectively result in the syringe and the PFT device simultaneously being characterized, calibrated, and/or validated based on first principles, rather than by reference to a standard.

As shown in FIG. 8, the gas analyzer 210 can produce the distorted "measured" representation of the "actual" concentration of the gas due to noise, nonlinearity, scalar errors, time dependencies, and/or any other source of measurement error. Such measurement errors can be modeled and/or extracted based on the known exponential behavior of a serial dilution.

Figure 9:
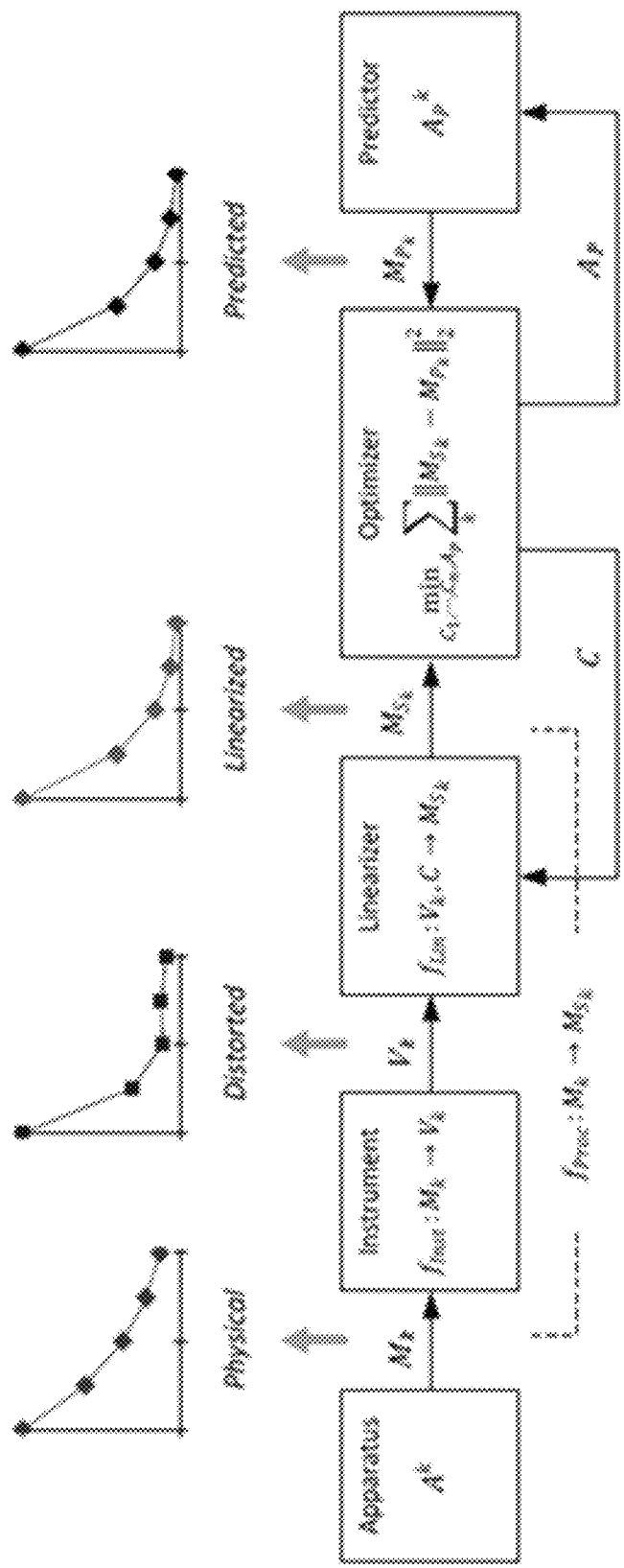
FIG. 9 illustrates further details of the method of simultaneously calibrating and/or validating a syringe and a gas analyzer of FIG. 7.

FIG. 9 illustrates further details of the method of simultaneously calibrating and/or validating a syringe and a gas analyzer, shown and described with reference to FIG. 7. Ultimately a predictor module can produce a representation of the dilution process $M_{P_k}$.

The syringe (referred to herein as the "apparatus" with reference to FIGS. 9 and 10) produces a physical series of concentrations $M_k$ according to mixing ratio A of the apparatus. The PFT device and/or gas analyzer (referred to herein as the "instrument" with reference to FIGS. 9 and 10) can return a distorted representation of the series of concentrations $V_k$. The instrument and linearizer module can be represented by a single function $f_{Proc}$ representing the gas analyzer, which converts physical concentrations $M_k$ into representative values $M_s$.

The linearizer module and an optimizer module can parameterize and resolve the decay rate $A_P$ of the syringe. Similarly stated, although the exponential behavior of the apparatus is known, the decay rate $A_P$ itself may not be known with sufficient accuracy, and can be resolved by the linearizer and optimizer modules. To resolve the decay rate $A_P$, the linearizer module and/or the optimizer module can use the distorted representation of the series of concentrations $V_k$ as a reference to resolve a set of coefficients C that result in the linearizer module producing a set of exponentially related values $M_{S_k}$. Similarly stated, the coefficients C effectively linearize $f_{Proc}$. Thus, the linearizer function $f_{Lin}$ is the inverse of the instrument function $f_{Inst}$.

The exponentially related values $M_{S_k}$ produced by the linearizer may have a decay rate different from the decay rate physically produced by the apparatus $M_k$, but contain decay rate information from the apparatus and can provide a decay rate reference for the optimization module. The optimization module can search for a set of coefficients C and a predicted decay rate parameter $A_P$ that minimize the least square difference between the set of exponentially related values $M_{S_k}$ and the set of values representing the dilution process $M_{P_k}$. The optimization module can employ any suitable search algorithm to produce the set of coefficients C using any suitable regression analysis. As $M_{S_k}$ converges to $M_{P_k}$ the linearized values $M_S$ will be as exponentially related as the linearization function $f_{Lin}$ will allow, and the decay rate parameter $A_P$ produced by the predictor module will match the decay rate of $M_S$, in a least square sense. Thus, the predictor module can produce the exponentially related reference for the coefficient C search and the linearizer module can produce the decay rate reference for the predictor module's parameter search. It should be noted that the coefficients C and decay rate parameter $A_P$ are solved simultaneously, not in an alternating manner. As the optimizer module iterates, the measured values $M_S$ become more exponentially related and the decay rate of the predicted value $M_P$ converges to a fixed value.

Concisely, the optimization process calculates N number of coefficients C and predicted decay rate $A_P$ according to the following:

$$\lim_{N \to \infty} f_{Proc}(M_k, C_1, C_2 \ldots C_N) = M_{S_k} = M_{P_k} = A_P^k = (\lambda A)^k \quad (6)$$

According to equation (6), $f_{Proc}$ is an eigenfunction over A of the apparatus's function $A^k$. If $f_{Proc}$ is a set of exponential values of decay rate A, $f_{Proc}$ will return a set of exponential values, but with a decay rate of A scaled by $\lambda$. Thus, the optimization module can include or be operable to execute an eigenfunction solver that solves for the nearest eigenfunction that satisfies equation (6).

In the instance where the optimization module returns a set of coefficients C that make $f_{Proc}$ linear, then $\lambda=1$ and $A_P=A$. In such an instance, the mixing coefficient A of the apparatus and the inverse of the instrument's distortion $f_{Inst}$ are also known or solved, resulting in both the apparatus and the instrument being fully characterized. It should be noted, however, that in the process shown in FIG. 9 there exists an infinite number of possible eigenfunctions for $A^k$. Similarly stated, there exist an infinite number of possible nonlinearities of $f_{Proc}$ that satisfy equation (6) and therefore, the optimizer module is not fully constrained.

FIGS. 7-9 and equation (6) have thus far been described with reference to serial dilution. Equation (6), can be fully constrained by considering serial concentration, as described with reference to FIGS. 5 and 6 in addition to serial dilution as described with reference to FIGS. 7 and 8. Similarly stated, the apparatus has the capability to perform two separable mixing modes, serial dilution and serial concentration, characterized by two separable models, $1-A^k$ (concentration) and its complement $A^k$ (dilution). In some instances, the mixing ratio, A can also be independent for concentration and dilution (e.g., the first stop 130 and/or the second stop 140 can be moved between a dilution phase and a concentration phase), such that the models can be expressed as $A_D^k$ for dilution and $1-A_U^k$ for concentration.

Figure 10:
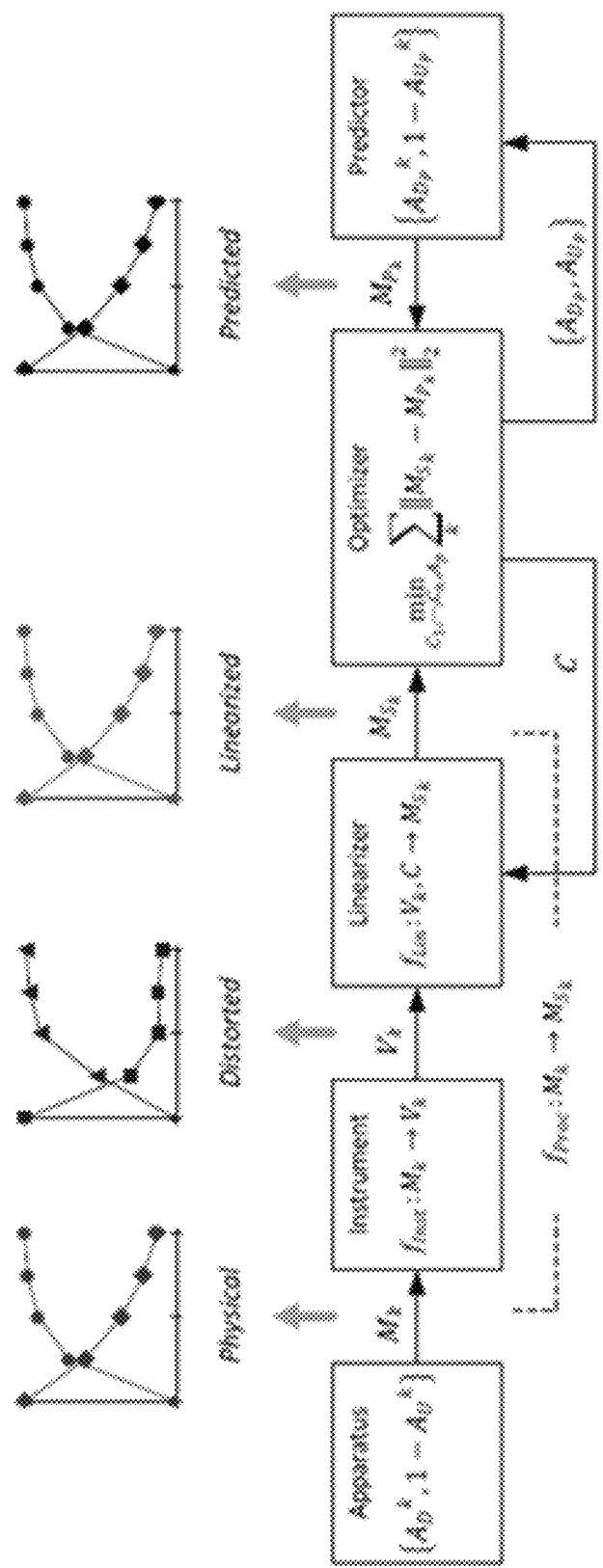
FIG. 10 depicts a method of simultaneously calibrating and/or validating a syringe and a gas analyzer using serial dilution and serial concentration, according to an embodiment.

FIG. 10 is similar to FIG. 9, but depicts a process in which a predictor module can produce a representation of the dilution and/or concentration process $M_{P_k}$ based on both a serial dilution, noted by the subscript D (e.g., $A_D^k$) and serial concentration, noted by the subscript U (e.g., $A_U^k$). The method depicted in FIG. 10 can produce a single set of linearization coefficients C for both the concentration and dilution modes. As a result, the process will converge on a set of linearization coefficients C such that $f_{Proc}$ converges to the nearest eigenfunction of both mixing modes. The only eigenfunction that exists for both mixing models is the function $M_S=M_k$, the linear case.

$f_{Proc}$ will always converge in the fully constrained algorithm to a linear function. It follows that $f_{Proc}$ with coefficients C will converge to the inverse of the instrument function $f_{Inst}$, which introduced distortion into the values V. If $f_{Proc}$ is linear, then by definition the decay rates in $M_s$ match the physical decay rates of M. Consequently, the optimizer module will force the predictor module's parameters $A_{D_P}$ and $A_{U_P}$ to converge to the physical decay rates $A_D$ and $A_U$, respectively, which are the mixing ratios of the apparatus. These physical mixing ratios are the attributes that the process is intended to determine.

The fully constrained optimization process calculates N number of coefficients C and both predicted decay rates $A_{D_P}$ and $A_{U_P}$ according to the following:

$$\lim_{N \to \infty} \begin{vmatrix} f_{Proc}(\{M_{D_k}, M_{U_k}\}, C_1, C_2 \ldots C_N) = \{A_D^k, 1 - A_U^k\} \\ \text{and} \\ A_{D_P} = A_D, A_{U_P} = A_U \end{vmatrix} \quad (7)$$

$$\forall M \; 0 < M < 1$$

Applying equation (7), not only are the mixing ratios of the apparatus determined, but also the nonlinearity of the instrument is determined via the linearization function $f_{Lin}$ and its associated coefficients C. Both the apparatus and instrument are characterized by this process.

It should be understood that where methods and equations describe exponential operations having the form $M=A^k$, one skilled in the art would understand that such methods and equations can be configured to process the recursive definition of the exponential (e.g., $M_k=A M_{k-1}$), such as is shown and described above with reference to equation (2). In some instances, methods and equations described herein, altered to process the recursive definition of exponentials can eliminate constraints related to, for example, the order in which serial dilution and serial concentration are performed. One skilled in the art would understand that such equations would otherwise produce the same results and can be proven by similar analysis as described in further detail below.

The method shown and described with reference to FIG. 10 can be mathematically proven as follows. According to equations (6) and (7), only one eigenfunction exists for both mixing functions $A_D^k$ and $1-U^k$. Restated, the eigenfunction spaces of $A_D^k$ and $1-A_U^k$ intersect at one singular point: $f$: $x \to x$, the linear case. (The linear function $f$: $x \to x$ (or $f$: $x \to \lambda x$) is an eigenfunction of any function.) The method depicted in FIG. 9 includes solving for a set of coefficients C such that $f_{Proc}$ is an eigenfunction of $A_D$ and $A_U$, according to equation (7). Moreover, the method depicted in FIG. 9 allows for the eigenfunction of $A_D$ and $A_U$ to be solved over any mixing coefficient(s) presented by the apparatus. The eigenfunctions of both mixing models $A_D^k$ and $1-A_U^k$ can be described as:

$$\mathcal{F}(A_D^k, M) = (\lambda_D A_D)^k = A_D^k + f(M) \quad (8)$$

$$\mathcal{F}(1-A_U^k, M) = 1 - (\lambda_U A_U)^k = 1 - A_U^k + f(M) \quad (9)$$

Solving for $f(M)$ gives:

$$f(M) = (\lambda_D A_D)^k - A_D^k \quad (10)$$

$$f(M) = A_U^k - (\lambda_U A_U)^k \quad (11)$$

Equations (10) and (11) can be equated to the same function $f(M)$ because both mixing models (concentration and dilution) are operated on by only one function $f_{Proc}$, which occurs in the M, or concentration, domain as shown in FIG. 9. Applying equations (2) and (3), $M=A_D^k$ and $M=1-A_U^k$, equations (10) and (11) can be transformed from the k domain into the M domain:

$$f(M) = M^{\frac{ln(\lambda_D A_D)}{ln(A_D)}} - M \quad (12)$$

$$f(M) = 1 - M - (1-M)^{\frac{ln(\lambda_U A_U)}{ln(A_U)}} \quad (13)$$

Equating equations (12) and (13) in the M domain gives:

$$M^{\frac{ln(\lambda_D A_D)}{ln(A_D)}} = 1 - (1-M)^{\frac{ln(\lambda_U A_U)}{ln(A_U)}} \quad (14)$$

Equation (14) defines the intersection of the eigenfunction spaces over A of $A_D^k$ and $1-A_U^k$. It follows from equations (6) and (7), that $\lambda_D=1$ and $\lambda_U=1$ satisfy equation (14). The solution to the system of equations (15) shows that $\lambda_D=1$ and $\lambda_U=1$ is the only possible solution that satisfies equations (14), which proves the assertion of equation (7).

$$M^{\frac{ln(\lambda_D A_D)}{ln(A_D)}} = 1 - (1-M)^{\frac{ln(\lambda_U A_U)}{ln(A_U)}} \quad (15)$$

$$\frac{d}{dM}\left(M^{\frac{ln(\lambda_D A_D)}{ln(A_D)}}\right) = \frac{d}{dM}\left(1 - (1-M)^{\frac{ln(\lambda_U A_U)}{ln(A_U)}}\right)$$

$$\frac{d^2}{dM^2}\left(M^{\frac{ln(\lambda_D A_D)}{ln(A_D)}}\right) = \frac{d^2}{dM^2}\left(1 - (1-M)^{\frac{ln(\lambda_U A_U)}{ln(A_U)}}\right)$$

$$\frac{d^3}{dM^3}\left(M^{\frac{ln(\lambda_D A_D)}{ln(A_D)}}\right) = \frac{d^3}{dM^3}\left(1 - (1-M)^{\frac{ln(\lambda_U A_U)}{ln(A_U)}}\right)$$

Equation (16) represents the solution to the system of equations (15), following a significant amount of algebraic manipulation due to the third order nature of the problem.

$$\{\lambda_D, \lambda_U, A_D, A_U\} = \quad (16)$$

$$\begin{cases} \lambda_D = 1, \lambda_U = 1, A_D \neq 1, A_U \neq 1, & \forall M, M \neq 0 \land M \neq 1 \\ \lambda_D \in \mathbb{R}, \lambda_U \in \mathbb{R}, A_D \neq 1, A_U \neq 1, & M = 0 \lor M = 1 \end{cases}$$

Equation (16) constrains the domain of equation (7) to $0<M<1$, the maximum normalized range of the measurement. Accordingly, $\lambda_D=1$ and $\lambda_U=1$ is the only solution that satisfies equation (7).

Returning to FIGS. 5, 7, 9, and 10, it should be understood that serial dilutions and/or concentrations of a test gas can be expelled from a syringe (e.g., the syringe 100) into a PFT device to validate, calibrate, and/or linearize the PFT device 200. Thus, each time the syringe is moved into a minimum-volume configuration, the PFT device 200 can produce and/or record a measured concentration of the gas expelled into the PFT device. A minimum of three serial concentrations and/or three serial dilutions can be used to characterize the linearity of the PFT device 200 and/or produce the representation of the concentration/dilution process $M_{P_k}$ as described above. Similarly stated, the methods described with reference to FIGS. 5, 7, 9, and 10 can allow for a dilution mixing ratio, a concentration mixing ratio and/or device linearity, to be determined based on the measured concentrations of the test gas. In some embodiments, the PFT device 200 can be calibrated by calculating and/or applying a correction factor to the PFT device (e.g., adjusting an offset, gain, and/or linearity of the PFT device) based on deviations between measured concentrations and predicted concentrations $M_{P_k}$. In other embodiments, the PFT device 200 can be validated and/or fail validation based on a comparison between measured concentrations and predicted concentrations. For example, after calibration and/or to validate a PFT device, one or all measured concentrations of the test gas and/or measured concentrations of subsequent mixtures of test gas applied to the PFT device may be within 0.5% of actual and/or predicted concentrations.

Traditionally, PFT equipment is calibrated at the time of manufacture and validated in the field. Due to the expense and unavailability of precision gas mixtures, it has generally not been possible to accurately validate, let alone calibrate, PFT equipment in the field. Furthermore, traditionally there has been large device-to-device variability of deployed PFT equipment, suggesting that accurate calibration of PFT equipment has not previously been possible at all. Unlike existing devices and/or methods purporting to calibrate and/or validate PFT equipment using precision gas mixtures and/or "standardized" dilutions of a gas mixture, the methods and apparatus described herein do not rely on precision mixtures of gas, or even devices able to produce an accurate mixing ratio. Rather, the methods and apparatus described herein are able to accurately validate and/or calibrate PFT equipment at time of manufacture and/or in the field with a single test gas source containing an arbitrary mixture of test gas and a syringe suitable to consistently draw the same volume. Similarly stated, methods and apparatus described herein are suitable to calibrate and/or validate PFT equipment by precisely and repeatedly producing the same volumetric displacement, rather than producing an absolutely accurate volumetric displacement. Accordingly, the apparatus and methods described herein are generally suitable for use on a wide range of PFT equipment, can be used to validate and/or calibrate PFT equipment such that the PFT equipment can confidently produce accurate physiologic data and can reduce or eliminate device-to-device variability.

Furthermore, the PFT device can be operable to identify testing irregularities and/or instrument irregularities. For example, industry standard criteria (e.g., exhalation length, exhalation volume, exhalation pattern, etc.) can be used to determine whether irregularities in a PFT are the likely result of patient and/or technician error. Additionally, the PFT device can detect instrument irregularities when, for example, the PFT device has not been recently (within predetermined period of time) calibrated/validated, when PFT results are consistent with a properly performed test, when PFT irregularities are consistent with a calibration error, etc. When an instrument irregularity is detected, an alert can be generated to instruct a technician to correct an error with an instrument and/or to prevent the technician from performing tests with the PFT device. For example, when an instrument irregularity is detected, the technician can be instructed to calibrate the PFT device, perform maintenance on the PFT device, initiate a service call, or take any other suitable action. When a testing irregularity is detected, the technician can be instructed to ask the patient to re-perform the test, alternate a coaching instruction for the patient (e.g., instruct the patient to exhale slower, faster, more forcefully, etc.), attend remedial training, that the patient is too ill to perform the PFT, or take any other suitable action.

While various embodiments have been described above, it should be understood that they have been presented by way of example only, not limitation, and various changes in form and details may be made. For example, although some embodiments describe PFT devices, in some instances, the syringes and/or methods described herein are suitable to validate and/or calibrate other devices that measure gas concentration. As another example, some embodiments describe PFT devices with gas analyzers and/or volume sensors. It should be understood, however, that unless the context clearly dictates otherwise, some embodiments of PFT devices may not include one or more described components (e.g., a volume sensor). As yet another example, some embodiments describe a syringe with a compliance feature. It should be understood that compliance features described herein can be integral to a syringe and/or removeably coupled to a syringe. For example, a compliant adapter configured to be removeably coupled to a PFT device and a syringe such that the adapter-syringe system has a compliance similar to that of a human subject should be understood as a syringe including an adapter.

Where methods described above indicate certain events occurring in certain order, the ordering of certain events may be modified. Additionally, certain of the events may be performed concurrently in a parallel process when possible, as well as performed sequentially as described above. It should further be understood that methods described herein may be partially and/or entirely computer implemented. Similarly stated, where events of methods are described herein, it should be understood that these events may be carried out, performed, and/or caused to be performed by a processor executing non-transitory code. Any portion of the apparatus and/or methods described herein may be combined in any combination, except mutually exclusive combinations. The embodiments described herein can include various combinations and/or sub-combinations of the functions, components and/or features of the different embodiments described.

Some embodiments described herein relate to calibrating and/or validating PFT equipment. Some such embodiments can further include recording, storing, and/or reporting PFT characterization and/or calibration result measurements. Such embodiments can further include suitable equipment (e.g., computers, servers, internet access, intranet access, cloud access, etc.) for recording, storing, and/or reporting such information. Such embodiments can also be operable to store and/or report PFT device specifications and/or physiologic testing capabilities (e.g., spirometry, nitrogen washout, $D_{LCO}$, plethysmography, etc.) and be operable to alert the operator in the event that the PFT equipment does not include a valid verification prior to testing patients (e.g., if the PFT equipment is out of calibration, has an expired calibration/validation, and/or the PFT equipment is not capable of measuring a patient with clinically meaningful accuracy and/or precision).

Some embodiments described herein refer and/or relate to modules. A module can be or include hardware and/or software (e.g., stored in memory or executing on a processor) operable to perform the referenced functions.

Some embodiments described herein, such as embodiments referring or relating to modules can relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

What is claimed is:

1. A method, comprising:
coupling a port of a syringe to a pulmonary function test device, the syringe having a housing, a piston, and a compensator such that the syringe has a fluid dynamic compliance of at least 1 L atm$^{-1}$;
transferring gas between the pulmonary function test device and the syringe; and
validating the pulmonary function test device based at least in part on a measurement of the gas transferred between the pulmonary function test device and the syringe.

2. The method of claim 1, wherein the pulmonary function test device includes a tank of pressurized gas and a demand valve configured to supply gas from the tank at or near atmospheric pressure to a human subject.

3. The method of claim 1, wherein:
the transferring gas between the pulmonary function test device and the syringe includes transferring gas from the pulmonary function test device to the syringe, the pulmonary function test device including a demand valve, the compensator configured to simulate dynamic compliance of a respiratory system of a human subject such that the transferring gas from the pulmonary function test device to the syringe includes gas being supplied to the syringe at or near atmospheric pressure.

4. The method of claim 1, wherein the pulmonary function test device is validated to perform nitrogen wash-out tests.

5. The method of claim 1, wherein the pulmonary function test device is validated to perform $D_{LCO}$ tests.

6. The method of claim 1, wherein the transferring gas between the pulmonary function test device and the syringe includes:
drawing a test gas from the pulmonary function test device, the test gas stored in a tank of pressurized test gas and regulated to atmospheric pressure via a demand valve;
mixing the test gas drawn from the pulmonary function test device with gas contained within the syringe to form a gas mixture;
injecting the gas mixture into the pulmonary function test device; and
measuring a concentration of the test gas in the gas mixture.

7. The method of claim 1, further comprising:
drawing a test gas from a pressurized gas source into the syringe such that the test gas is mixed with gas in a dead-space volume of the syringe to form a first mixture;
injecting the first mixture into the pulmonary function test device;
measuring a concentration of the test gas in the first mixture;
drawing the test gas from the pressurized gas source into the syringe such that the test gas is diluted with gas from the first mixture in the dead-space volume of the syringe to form a second mixture; and
measuring a concentration of the test gas in the second mixture, the validation of the pulmonary function test device being based at least in part on the measurement of the concentration of the test gas in the first mixture and the measurement of the concentration of the test gas in the second mixture.

8. A syringe, comprising:
a housing;
a piston moveably disposed within the housing, when the piston is in a first position, the piston and the housing collectively defining a first working volume, when the piston is in a second position, the piston and the housing collectively defining a second working volume; and
a port, the piston configured to discharge, through the port, gas having a volume equal to a difference between the first working volume and the second working volume when the piston is moved from the first position to the second position,
the syringe having a fluid dynamic compliance of at least 1 L atm$^{-1}$.

9. The syringe of claim 8, further comprising a servo-mechanism coupled to the piston and configured to move the piston in response to a change in pressure at the port to provide the fluid dynamic compliance.

10. The syringe of claim 8, further comprising an elastomeric diaphragm disposed on the housing and in fluid communication with a pulmonary function test device to provide the fluid dynamic compliance.

11. The syringe of claim 10, wherein the housing defines an opening to atmosphere, located between the port and the piston, the elastomeric diaphragm disposed over the opening such that the elastomeric diaphragm deflects when pressure changes at the port.

12. The syringe of claim 10, wherein an entirety of the port is constructed of an elastomeric material having a dynamic compliance of at least 1 L atm$^{-1}$.

13. The syringe of claim 10, wherein the diaphragm constructed of elastomeric rubber having a thickness of less than 7 mm and a surface area of at least 20 cm$^2$.

14. The syringe of claim 8, wherein the syringe has a dynamic compliance less than 3 L atm$^{-1}$.

15. The syringe of claim 8, wherein the port is a hollow body having openings covered by an elastomeric material such that gas flowing through the port at non-atmospheric pressure causes the elastomeric material to deflect.

16. The syringe of claim 8, further comprising an elastomeric bellows configured to provide the dynamic compliance of at least 1 L atm$^{-1}$.

17. The syringe of claim 8, further comprising an agitator disposed within the housing, the agitator configured to be mechanically energized by gas flowing inward through the port, the agitator configured to mix gas disposed within the housing.

18. The syringe of claim 8, further comprising:
a heat sink coupled to the housing and having a surface area at least three times greater than a surface area of the housing.

19. The syringe of claim 8, further comprising:
a heat sink coupled to the housing and having a surface area at least three times greater than a surface area of the housing and a perimeter contact area at least three times less than a perimeter contact area of the housing.

20. A system, comprising:
a syringe having a dynamic compliance of at least 1 L atm$^{-1}$; and
a pulmonary function test device configured to be coupled to a pressurized source of a test gas and configured to be coupled to the syringe such that the syringe can draw gas from the pressurized source, the pulmonary function test device including:

a volume sensor configured to measure a volume of gas moving between the pulmonary function test device and the syringe; and a gas analyzer configured to measure a concentration of the test gas expelled into the pulmonary function test device from the syringe.

21. The system of claim 20, wherein the volume sensor includes a flow rate sensor and a processor configured to integrate flow rate over time to measure volume.

22. The system of claim 20, wherein the pulmonary function test device includes a demand valve configured to supply test gas at or near atmospheric pressure to a human respiratory system, the syringe configured to simulate the human respiratory system such that the demand valve supplies test gas to the syringe at or near atmospheric pressure.

23. The system of claim 20, wherein:
the syringe is configured to mix test gas drawn from the pressurized test gas source with gas disposed in a dead-space volume of the syringe to form a gas mixture; and
the gas analyzer is configured to measure a concentration of the gas mixture.

24. The system of claim 20, wherein the syringe is configured to move a standard volume of gas such that the syringe is configured to validate the measurement by the volume sensor of the volume of gas moving between the pulmonary function test device measured and the syringe.

25. The system of claim 20, wherein the syringe is configured to perform a ratiometric dilution of the test gas such that the syringe is configured to validate the measurement of the concentration of the test gas measured by the gas analyzer.

26. The system of claim 20, wherein:
the syringe is configured to perform serial dilutions of the test gas with a fixed dilution ratio;
the gas analyzer is configured to measure a concentration of test gas for each dilution from the serial dilutions; and
the syringe and the gas analyzer are collectively configured to simultaneously determine the fixed dilution ratio of the syringe and determine the distortion function of the gas analyzer based on the measurements of the concentration of the test gas from each dilution from the serial dilutions.

27. The system of claim 20, wherein:
the syringe is configured to perform serial concentrations of the test gas with a fixed concentration ratio;
the gas analyzer is configured to measure a concentration of test gas for each concentration from the serial concentrations; and
the syringe and the gas analyzer are collectively configured to simultaneously determine the fixed concentration ratio of the syringe and determine the distortion function of the gas analyzer based on the measurements of the concentration of the test gas from each concentration from the serial concentrations.

28. The system of claim 20, wherein the syringe includes a diffusion barrier.

* * * * *